United States Patent
Gui et al.

(10) Patent No.: US 6,635,224 B1
(45) Date of Patent: Oct. 21, 2003

(54) ONLINE MONITOR FOR POLYMER PROCESSES

(75) Inventors: John Yupeng Gui, Niskayuna, NY (US); James Manio Silva, Clifton Park, NY (US); James Claude Carnahan, Schenectady, NY (US); Hugh Harrison Layer, Mt. Vernon, IN (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/183,698

(22) Filed: Oct. 30, 1998

(51) Int. Cl.$^7$ .................. G01N 21/00; G01N 31/00; G01N 33/00
(52) U.S. Cl. ............. 422/62; 422/68.1; 422/82.01; 422/82.02; 422/82.05; 422/82.06; 422/82.07; 422/82.08; 422/82.09; 436/34; 436/43; 436/52; 436/85
(58) Field of Search ............ 422/62, 68.1, 82.01, 422/82.02, 82.05–82.09; 356/246; 250/343; 436/34, 43, 50, 52, 55, 85, 164, 171, 174, 177–179

(56) References Cited

U.S. PATENT DOCUMENTS

| | | | | |
|---|---|---|---|---|
| 4,717,827 A | * | 1/1988 | Harvey ................. | 250/343 |
| 5,065,336 A | * | 11/1991 | Buchelli ................. | 364/499 |
| 5,114,861 A | * | 5/1992 | Silva et al. ............. | 436/85 |
| 5,907,108 A | * | 5/1999 | Garcia-Rubio et al. .. | 73/863.21 |
| 6,072,576 A | * | 6/2000 | McDonald et al. ........ | 356/300 |

FOREIGN PATENT DOCUMENTS

WO 98/29787 * 7/1998

OTHER PUBLICATIONS

L. G. Weyer Making Light Work: Adv. Near Infrared Spectrosc., Int. Conf. Near Infrared Sepctrosc. 1992, I. Murray et al. Ed., VCH: Weinheim, Germany, pp. 430–437.*
R. O. Welty SPE J. 1965, 21, 774–777.*
I. S. Volchek et al, Plast. Massy 1967, 55–7.*
A. Hirsch et al, Can. Spectrosc. 1967, 12, 101–104.*
S. Y. Shchegolev et al, Opt. Spektrosk. 1971, 31, 794–802.*
K. A. Johnson et al, Anal. Biochem. 1984, 136, 192–194.*
T. Kourti et al, ACS Symp. Ser. 1987, 332, 242–255.*
M. Bernardini et al, Riv. Ital. Sostanze Grasse 1987, 64, 557–61.*
T. Kourti et al, Polym. Mater. Sci. Eng. 1990, 62, 301–305.*
W. Lau et al, Macromolecules 1992, 25, 4448–4449.*
W. W. Yau et al, Int. J. Polym. Anal. Charact. 1996, 2, 151–171.*
R. A. Fidler et al, ANTEC, 1991, 49th, 850–855.*
R. W. Jones et al, Process Control Qual. 1993, 4, 253–260.*
A. Khettry et al, ANTEC 1995, 53rd, 2824–2831.*
M. Hosono et al, Bull. Inst. Chem. Res., Kyoto Univ. 1973, 51, 104–117.*

(List continued on next page.)

*Primary Examiner*—Arlen Soderquist
(74) *Attorney, Agent, or Firm*—Toan P. Vo; Patrick K. Patnode

(57) ABSTRACT

This invention provides an online polymer monitoring apparatus for rapid determination of molecular weight and/or size, and/or other properties of importance to the polymer quality. The apparatus uses fast sample extraction, preparation and delivery techniques to convert complex polymer sample solution into the diluted polymer analyte solution. This analyte solution is then passed through the flow-through detectors for measurement of the polymer molecular weight, the polymer concentration and/or the identification and concentrations of the selected species of importance to the polymer quality. The continuous stream of the above measurement data, thus, allows accurate determination the status of the polymer for many polymer containing process streams, such as an ongoing polymerization reaction mixture, polymer resin fluid, melt or solid polymer flow.

35 Claims, 16 Drawing Sheets

OTHER PUBLICATIONS

C. Kiparissides et al, Can. J. Chem. Eng. 1980, 58, 65–71.*
R. L. Zollars J. Colloid Interface Sci. 1980, 74, 163–172.*
U. Budde et al, Angew. Makromol. Chem. 1988, 161, 195–204.*
T. Kourti et al, Adv. Chem. Ser. 1990, 227, 105–139.*
T. Takebe et al, J, Chem. Phys. 1990, 92, 1386–1396.*
A. Brandolin et al, ACS Symp. Ser. 1991, 472, 64–85.*
D. F. Nicoli et al, ACS Symp. Ser. 1991, 472, 86–97.*
J. C. Thomas ACS Symp. Ser. 1991, 472, 98–105.*
Y. Takeuchi Keiso 1993, 36, 17–20.*
P. D. Gossen et al, J. Colloid Interface Sci. 1993, 160, 24–38.*
S. K. Menon et al, Polym. Sci. 1994, 2, 749–754.*
M. G. Hansen et al, Annu. Tech. Conf.—Soc. Plast. Eng. 1994, 52, 2220–2226.*
C. Wu et al, Process Control Qual. 1996, 8, 1–23.*
V. Liotta et al, Am. Control Conf., Proc. 15th 1997, 2, 1172–1176.*
S. Li et al, J. Polym. Sci. B Polym. Phys.1997, 35, 2935–2943.*
F. H. Florenzano et al. Macromolecules 1998, 31, 7226–7238, Oct. 1998.*
M. Martin Chromatographia Jul. 1982, 15, 426–432.*
A. Penlidis et al, Polym. Process Eng. Mar. 1985, 3, 185–218.*
M. A. Haney J. Appl. Polym. Sci. Jul. 1985, 30, 3037–3049.*
O. Prochazka et al, J. Appl. Polym. Sci. Nov. 1987, 34, 2325–2336.*
A. H. Dekmezian et al, Anal. Chem. Mar. 1989, 61, 458–461.*
S. Kim et al, J. Polym. Sci. B: Polym. Phys. Feb. 1992, 30, 177–183.*
J. J. Kirkland et al, Anal. Chem. Apr. 1992, 64, 904–913.*
K. G. Suddaby et al, Makromol. Chem. Jul. 1993, 194, 1965–1974.*
P. D. Gossen et al J. Colloid Interface Sci. 1993, 160, 24–38.*
M. G. Hansen et al, Polym. Eng. Sci. Dec. 1994, 34, 1758–1766.*
J. Batra et al, Polym. Eng. Sci. Dec. 1994, 34, 1767–1772.*
A. C. van Asten et al, J. Chromatogr. A May 1995, 703, 245–263.*
M. G. Hansen et al. Tappi J. Sep. 1995, 78, 129–134.*
B. Badley et al, Macromol. Chem. Phys. Nov. 1996, 197, 3711–3728.*
H. Wang et al, Polym. Eng. Sci. Feb. 1997, 37, 363–376.*
M. Wakabayashi Idemitsu Giho Mar. 1997, 40, 296–301.*
K. E. Creasy AT–Process 1997, 2, 416–423.*
M. D. Zammit et al, Polymer Aug. 1997, 38, 4455–4468.*
S. Li et al, J. Polym. Sci. B: Polym. Phys. Dec. 1997, 35, 2935–2943.*
P. J. Wyatt J. Colloid Interface Sci. Jan. 1998, 197, 9–20.*

* cited by examiner

ONLINE MONITOR FOR POLYMER PROCESSES

BACKGROUND OF THE INVENTION

This invention relates to an online monitor for the continuous determination of the status of a polymer containing process stream through the measurement of polymer molecular weight and/or size and the measurement of composition and concentration of selected species such as monomers and endgroups. The monitor is used, inter alia, to detect the reaction endpoint of a polymer manufacturing process, to monitor polymer quality in a polymer containing process stream, or to perform polymer characterization in an industrial or laboratory setting.

Polymers are formed by a number of reactions, all of which involve the addition or condensation of monomers or other polymer blocks onto growing chains of repeating units. To illustrate, the formation of a polyester is depicted in the following reaction.

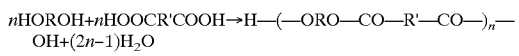

The degree of polymerization is represented by the number of repeating units in the chain, which is the integer n in the above reaction. Whether a polymer chain is formed by step-growth polymerization or chain-growth polymerization, the resulting polymers consist of a mixture of polymer molecules with a distribution of molecular weights. The average molecular weight and molecular weight distribution and/or the average size and size distribution of a polymer can be determined by gel permeation chromatography (GPC). For simplicity in the following discussion, the term "MWR" will be taken to mean the following: "weight average molecular weight or molecular size". Thus, the polymer MWR can be determined by GPC. Basic concepts in polymer science and technology are thoroughly reviewed by J. P. Flory, in Principles of Polymer Chemistry, Cornell University Press, 1953.

Polymer MWR can also be determined by techniques such as light scattering, viscosity, osmometry and freezing-point depression (unless noted otherwise, the term light scattering refers to steady state light scattering, as distinguished from dynamic light scattering.). For example, viscosity can be used to determine the polymer MWR of solutions of such polymers as polyesters and proteins or DNA. However, for a dispersed two-phase mixture such as an interfacial process polycarbonate reaction mixture, the solution viscosity is also dependent on the water/organic solvent ratio, the temperature, and the reactor agitation rate, which introduces inaccuracies into this method.

For biological polymers, determination of polymer MWR by viscosity measurement is not preferred. DNA is easily damaged and broken by the type of handling normally associated with viscosity measurements. For protein solutions, viscosity is only accurate for proteins in a random coil configuration. Secondary structure and the degree of denaturation of the protein affect the viscosity of the protein solution, which also depends on such factors as the solution pH, temperature, shear forces, intra- and intermolecular bonding and other factors, making viscosity a highly unreliable method for many types of biological polymers. The molecular weight of biopolymers has been determined in the laboratory by techniques such as SDS-gel electrophoresis, density gradient sedimentation, thin-layer gel chromatography, and viscoelasticity (relaxation time).

Polymer MWR is one of the most important factors that affect polymer properties. For many engineering thermoplastic polymers, as the polymer MWR increases, the mechanical properties of the polymer improve. For example, tensile strength, impact resistance, ductility, and other physical properties of the polymer are all improved with increasing polymer MWR. However, as the polymer MWR increases, the melt viscosity also significantly increases. When the melt viscosity becomes too high, melt processing the polymer becomes difficult or nearly impossible.

In polymer synthesis, the endpoint of a polymerization reaction can be defined as the point at which the polymer meets the desired specifications for all intrinsic polymer properties such as polymer MWR, dispersity, residual endgroup concentration(s), and residual monomer composition and concentration(s). To ensure that a polymerization reaction achieves its endpoint, one should have timely information about these intrinsic polymer properties, or the reaction process conditions such as pH, viscosity, temperature or pressure that are related to the intrinsic polymer properties, or a combination of both. The apparatus of this invention allows online monitoring of the following intrinsic polymer properties: polymer MWR and the concentration(s) of residual monomer(s) and/or endgroups.

In a polymerization reaction, polymer MWR is often the most important intrinsic polymer property to be achieved. In many cases, polymer MWR alone is sufficient to determine the polymerization reaction endpoint. However, in other cases, the reaction endpoint is defined by a specified polymer MWR and by other parameters such as the concentrations of residual monomer and/or endgroups. In such cases, the reaction endpoint must be determined with polymer MWR monitoring plus one or more additional measurements.

For example, for an interfacial polycarbonate manufacturing process, both polymer MWR and residual bisphenol-A (BPA) concentration are important quality parameters. Although a low level (<100 ppm) of BPA monomer in a polycarbonate reaction mixture has no significant effect on the polymer MWR, the presence of this level of monomer can influence the polymer quality and possibly limit its use in certain applications. Therefore, it is often desirable to include both polymer MWR and residual BPA concentration in the definition of the reaction endpoint for a polycarbonate polymerization reaction.

There are many physical and chemical properties of the reaction mixture besides the polymer MWR that change during the course of a polymerization. Current methods for detecting the reaction endpoint are based on one or more of these properties. For example, there are techniques that are based on the heat released during the reaction, decreases in the concentration of monomer, increases in the concentration of the byproducts of the reaction, the occurrence of wasteful side reactions, pH changes, droplet size (in interfacial polymerizations), decreases in end group concentrations, colorimetric assays, and light transmission through the reaction mixture.

For example, several techniques have been developed for detecting the reaction endpoint in interfacial polycarbonate polymerization, as reviewed by Silva and Fyvie in U.S. Pat. No. 5,114,861, which is incorporated herein by reference. These techniques include monitoring the heat release per unit phosgene delivered and monitoring the carbonate ion level in the reaction mixture. Both of these methods are based on detecting the effects of phosgene hydrolysis, a wasteful side reaction that occurs primarily after the polymerization is substantially complete. These techniques have two principal drawbacks. First, they require significant phosgene hydrolysis to occur before a clear endpoint signal can be detected. This means that significant losses in both raw materials and time must occur before the reaction is terminated. Secondly, significant phosgene hydrolysis can occur prior to the true reaction endpoint, due for example to an incorrect catalyst level. This can cause a false endpoint, which would lead to premature termination of the reaction, resulting in low quality polymer.

Attempts have also been made to monitor droplet size and the related dispersion properties by acoustic, focused beam reflectance, and dynamic scattering techniques. These methods have not succeeded because droplet size relates not only to the polymer MWR, but also many to other operational variables such as temperature, agitation rate, the volume ratio of aqueous and organic solvents and others. These factors can not always be completely controlled, which can lead to erroneous results.

U.S. Pat. No. 5,114,861 describes a method of reaction endpoint detection for interfacial polycarbonate polymerization reactions which measures the extent of apparent light transmission. This method is based on the effects of polymer MWR and endgroup concentrations on the polymer phase average droplet size, which influences the extent of apparent light scattering. Although this technique does not require significant phosgene hydrolysis to be effective, the detector signal is somewhat sensitive to the operating and thus these conditions must be compensated for or carefully controlled.

Inferring a reaction endpoint from process measurements which are indirectly related to the true polymer MWR is by its very nature imprecise. The measured properties such as the rate of heat release depend on a number of process variables in addition to the polymer MWR. In addition, the prior art methods of polymerization reaction endpoint detection are highly process- and equipment-specific. These methods, therefore, while somewhat effective for specific applications, are subject to serious errors if process or equipment changes are made.

Ensuring consistent polymer quality in a polymer containing process stream is also highly desirable. For example, if the polymer MWR of a polymer containing process stream that feeds a resin dryer falls below a specified level, dryer fusion can result, in which the polymer particles become plasticized as they are heated above their glass transition temperature. This results in agglomeration into large viscous polymer masses that can plug process equipment, which leads to extensive down time. A method of reliably and quickly monitoring the polymer MWR of a polymer containing process stream is thus essential to ensuring high productivity and consistent product quality.

Using light scattering and concentration measurements to determine polymer MWR in combination with GPC is acceptable in a laboratory environment. However, this method has not been applied to monitor the polymer MWR online in a manufacturing process because light scattering measurements require low polymer concentrations in solution and GPC leads to unacceptable measurement delays. In addition, both light scattering and GPC require that the analyte solution be free of particulates and bubbles, and exist as a single phase. Unfortunately, most manufacturing processes introduce particulates and bubbles into polymer containing process streams, and many processes involve multiple phases. Removal of these interfering materials typically requires procedures that introduce delays that are not consistent with the response time requirements of a monitor for monitoring and control of a rapidly changing system. None of the prior art methods of polymer process monitoring is adaptable to an online, continuous, system which produces no waste stream, does not result in loss of polymer due to sampling the polymer containing process stream, and is insensitive to changes in process conditions such as the agitation rate.

Consequently, there is a great need for a flexible, online monitor to monitor the status of both polymer containing process streams and polymerization reactions. Such a monitor must be applicable to a variety of polymer processes and provide continuous process data. When used as a reaction endpoint detector, such a monitor would allow control of the termination of the reaction at the correct time and not require the addition of reagents to the analyte stream, thereby allowing the analyte stream to be returned to the process. Such a device or method would enable continuous online monitoring of reaction status or endpoint for a variety of batch or continuous polymerization processes to ensure consistent polymer quality, reduced raw materials and energy usage, and increased productivity. Such a device would also enable continuous online monitoring of a polymer containing process stream and enable rapid quality control checks.

SUMMARY OF THE INVENTION

In one aspect, the present invention provides an online polymer monitoring apparatus for determination of polymer properties, comprising:

a) a flow through detector means having at least one inlet and one outlet, comprising at least one light scattering detector, at least one polymer concentration detector, and optionally additional detectors;

b) a sampling and delivery system for collecting a representative sample from a polymer containing process stream, having i) a first flow means having a first end connected to the polymer containing process stream and a second end connected to the detector means inlet;

ii) optionally a dilution means comprising a solvent source and a second flow means having a first end connected to the solvent source and a second end connected to the first flow means for delivering solvent to the first flow means;

iii) optionally a sample preparation means in association with the first flow means, which prepares the analyte solution from the representative sample by separating and/or filtering interfering materials;

iv) optionally, a means associated with the first flow means for controlling the flow of the representative sample from the polymer containing process stream to the detector means;

v) optionally, a third flow means for directing material from the outlet of the detector means to the polymer containing process stream; and vi) optionally, a circulation loop comprising a fourth flow means between the polymer containing process stream and the first flow means through which polymeric material is moved out of the polymer containing process stream and returned to the polymer containing process stream driven by a pumping and/or pressure differential mechanism; and c) means associated with the flow through detector means for calculating the polymer properties in the representative sample in response to data obtained by said detector means.

In another aspect, the present invention provides an online method for monitoring the status of a polymer containing process, which comprises:

a) collecting and preparing a sample online from a polymer containing process stream;

b) analyzing the collected and prepared sample by obtaining at least one of the following: the concentration responses of at least one polymer in said sample, the polymer light scattering responses of said sample, and/or the detector responses of the selected species in said sample;

c) inferring a polymer property from the results of step b).

DETAILED DESCRIPTION OF THE INVENTION

Specific preferred embodiments of the invention will now be described with reference to the schematic drawings contained in the figures.

Figure 1:
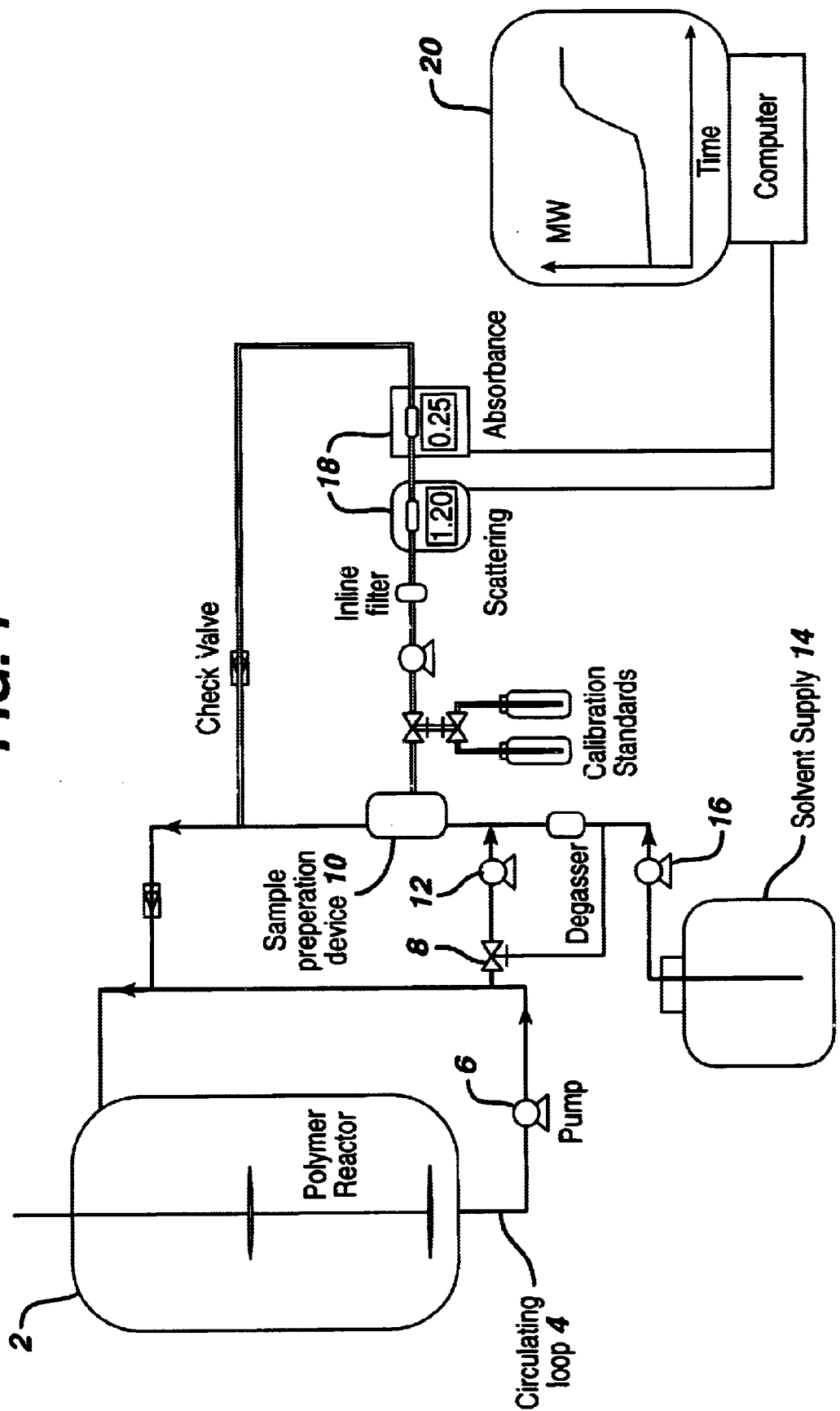
FIG. 1 is a schematic diagram of one embodiment of the online polymer monitoring system.

Referring to FIG. 1, the polymerization reaction takes place in a polymer reactor 2, to which is attached a circulating loop 4. Flow of liquid through the loop 4 is assisted by a pump 6. A three-way valve 8 allows the feeding of liquid from the loop 4 to a sample preparation device 10. Depending on the viscosity and pressure in the loop 4, the liquid feed rate is controlled by a pump 12 or pressure regulator. A solvent supply 14 feeds dilution solvent by means of a pump 16. The solvent supply 14 optionally includes a line connected to an inert gas source for degassing solvent in the solvent supply 14. The dilute polymer sample solution enters the sample preparation device 10 that separates and extracts polymer from interfering materials and provides the diluted, filtered polymer analyte solution to the detectors 18. A major portion of polymer sample solution exits the sample preparation device 10 and is recycled back into the loop 4, and a minor portion travels through the sample preparation device 10 and to the detectors 18. The detector 18 means in FIG. 1 includes a light scattering detector 18 and a concentration detector 18. In FIG. 1, the detectors 18 are depicted as arranged in series, but it is also acceptable for them to be arranged in parallel. The data generated by the detectors 18 are directed to a computer 20, which calculates polymer MWR from the data provided and displays such calculation(s) in a useful format. After passing through the detectors 18, the polymer solution may be disposed of or may be recycled back into the reactor 2 directly or through the circulation loop.

The initial part of this online polymer monitor is a rapid online sample preparation means that comprises a combination of selected sample preparation devices such as bypass filter(s), coalescer(s), centrifuge(s), inline filter(s) and degasser(s).

Figure 2:
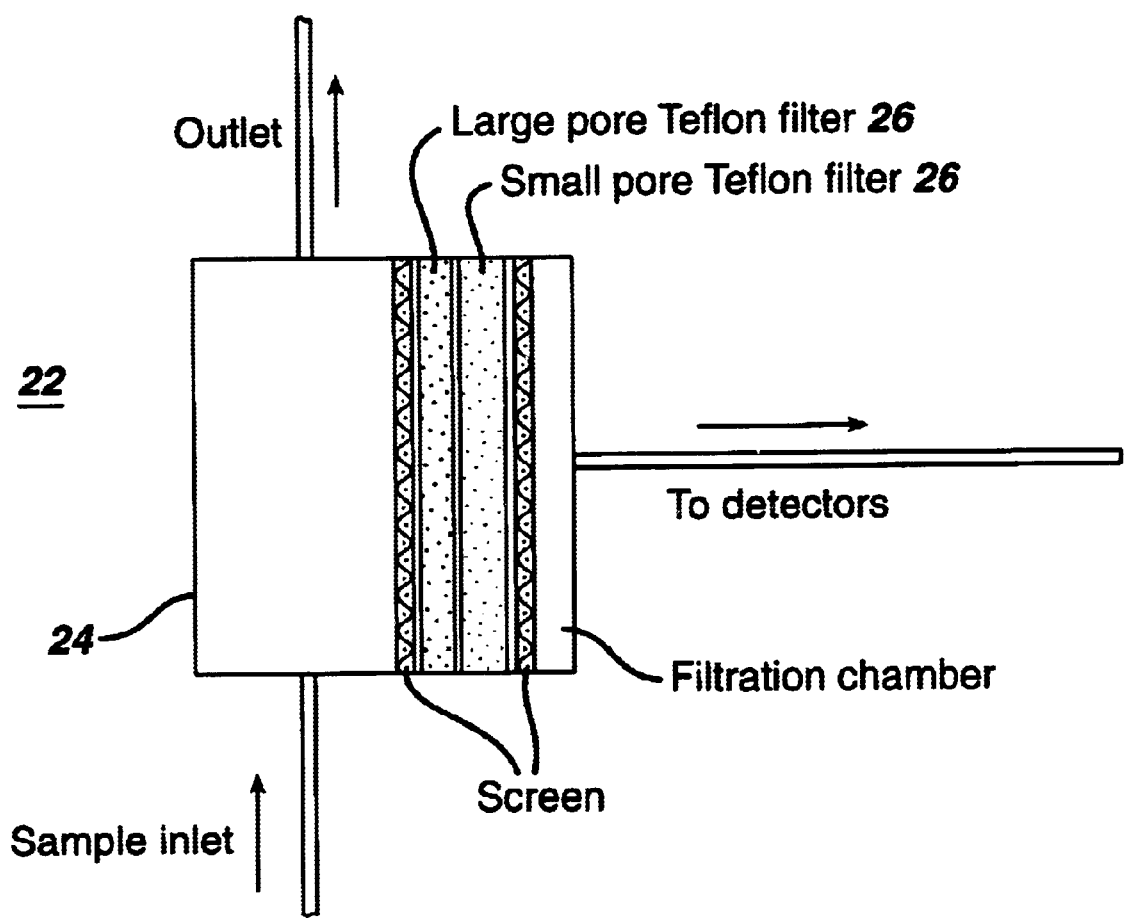
FIG. 2 is a schematic diagram of a bypass filter as a preferred sample preparation device.

One embodiment of the sample preparation device 10 is a phase separation bypass filter 22, as shown in FIG. 2. A phase separation bypass filter 22 is a simple and effective means for the extraction of polymer from a polymer containing process stream comprising two or more phases, such as polycarbonate in a solvent/aqueous process stream, and is preferred for this purpose. A suitable bypass filter 22 for the said polycarbonate process stream typically comprises a stainless steel body 24 and Teflon filtration elements 26 as shown in FIG. 2. The diluted sample stream passes across the filter and only the organic solvent phase passes through the Teflon filter elements 26. Water, inorganic salts and any particulates larger than the filter pore size do not pass through the filter elements 26. Furthermore, this by-pass filter is so designed so the sample enters the filter with swirling motion that acts as self-cleaning.

Figure 3:
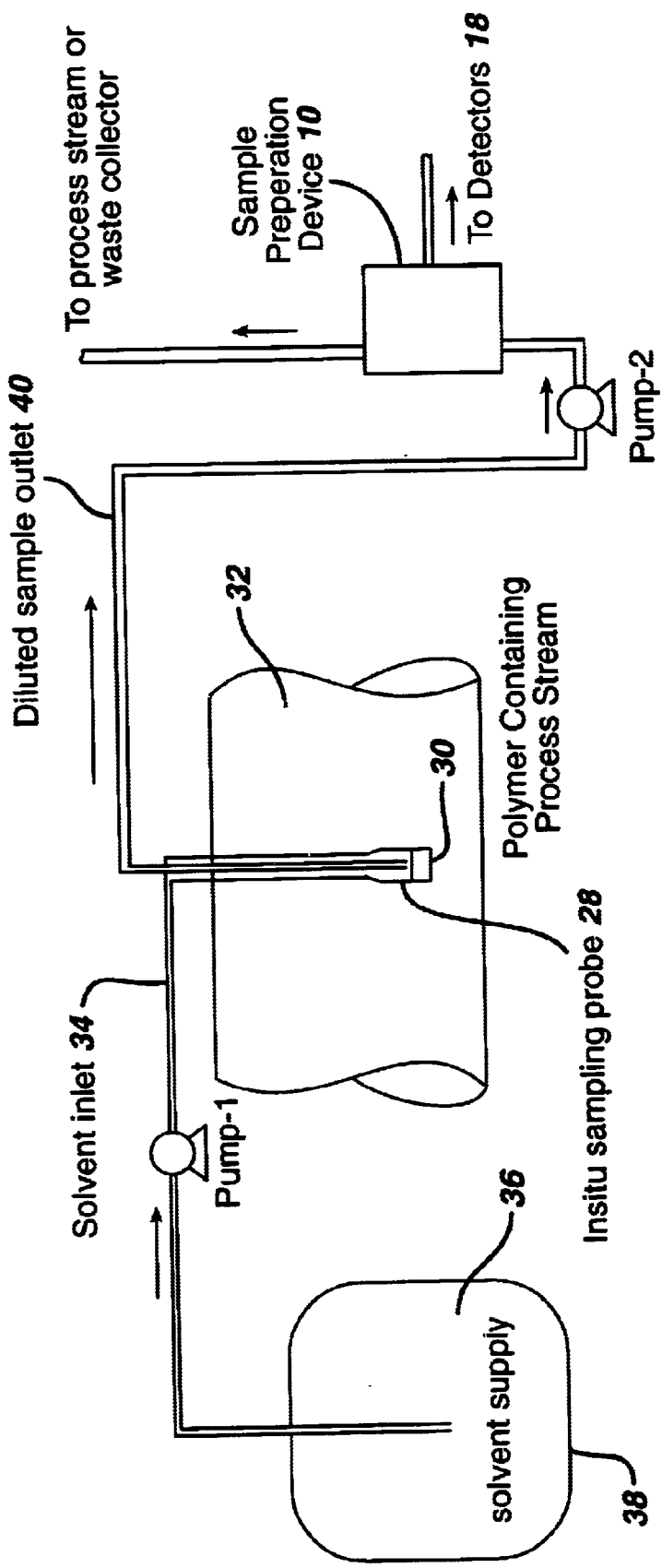
FIG. 3 is a schematic diagram of an online sampling apparatus with an in-situ sampling probe.
Figure 4A:
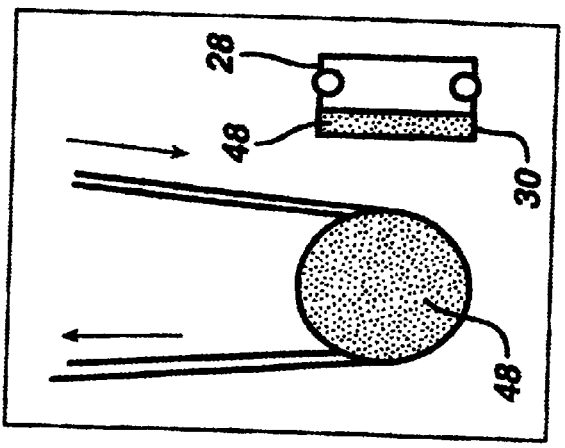
FIG. 4 (a–d) shows four different probe designs.
Figure 4B:
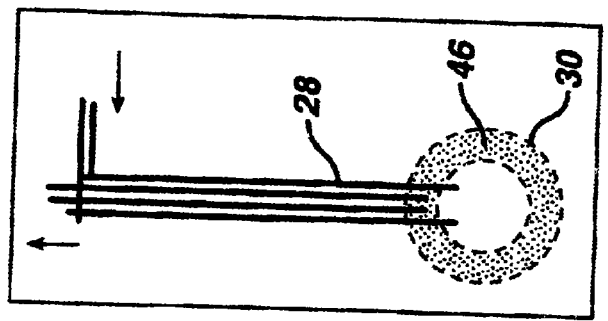
Figure 4C:
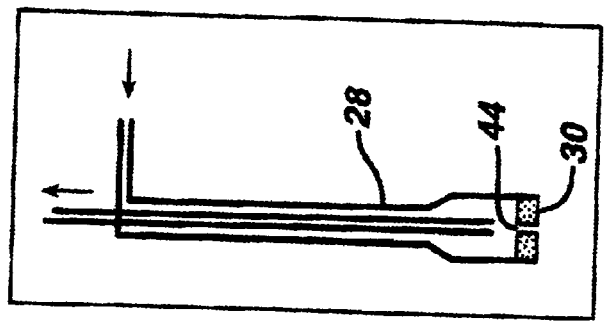
Figure 4D:
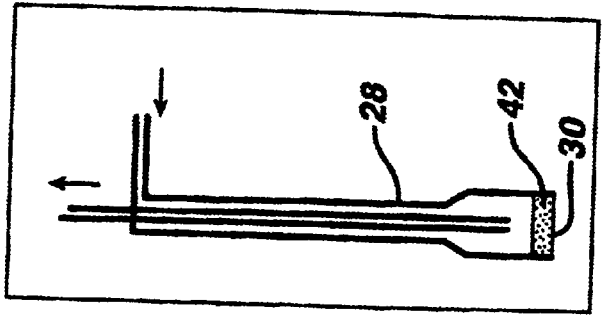

In another embodiment shown in FIG. 3, the sampling means includes an in situ sampling probe 28 located within the polymer containing process stream. The probe 28 has a first inlet means 30 open to the polymer sample solution 32, a second inlet 34 into which solvent 36 from the solvent source 38 flows, and an outlet means 40 which leads to the sample preparation device 10 or directly to detectors 18. The main advantage of the in-situ sampling probe 28 is that it typically has a much shorter sampling delay than the sampling method shown in FIG. 1. With an in-situ sampling probe 28, the sample solution 32 is diluted in the probe 28. Furthermore, the in-situ probe 28 can provide more consistent dilution than the regular sampling method. The in-situ probe 28 design and construction normally depends on sampling conditions and requirements such as the solvent 36 and sample flow rates, sample solution composition 32, sample solution viscosity, dilution factor, response time, and others. Illustrated in FIG. 4 are four sampling probes 28 in which the sample solution inlets 30 are made of flat porous material 42, one or more pinhole(s) 44, a porous sphere 46, and a flat membrane 48 as depicted in Diagrams A–D, respectively. Examples of porous materials are glass, metal and polymeric frits that have pore size greater than 100 microns. Most membrane materials are polymeric and have pore size less than 100 microns.

Probes suitable for use with the invention are hollow receptacles with a solvent inlet, a solution outlet and a flow-restricted inlet that allows material from the polymer containing process stream to enter the interior of the probe, without permitting passage of particulates. Optionally, a filter which also excludes droplets of a second phase may be used. The probe may be constructed of any material which is compatible with the solvents or phases to be used. Screens can be made of any material known in the art which are likewise compatible with the solvents or phases to be used and will function to reject undesired particulates and phases. Suitable screens are bare or chemically treated glass frits, polymeric frits, or other porous materials, which are readily apparent to those skilled in the art. The hydrophobicity of the screen or frit may affect the proportion of each phase which passes through in a two phase system. For example, a glass frit used with an aqueous/organic system will allow more of the aqueous phase to pass than of the organic phase since the glass is hydrophilic. As a consequence, the diluted sample solution can have a higher aqueous component than the actual process sample. The reverse could be expected to occur if a hydrophobic screen is used.

An appropriate diluting solvent enters the in situ sample probe interior from a solvent reservoir, controlled by a suitable flow metering device such as a pump. The flow of diluted analyte solution out of the outlet is controlled by a suitable flow metering device such as a pump with a higher flow rate than that of the first flow metering device. The difference between the two flow rates determines the net inflow of sample solution from the polymer containing process stream through the screen, and into the sample probe interior. A static mixer or other mixing device may be optionally used to mix the diluted solution in the sample probe.

For many polymer containing process streams in which conditions are simple (e.g., one phase, low solids level) and mild (e.g., low pressure and temperature), the in situ dilution sample probe and the sample preparation means can be combined by simply integrating appropriate filter elements into the screen, with or without a pre-screen. Usually, the in situ probe is designed to be placed in contact with a polymer containing process stream. An in situ sample probe with a simple screen can also be used in conjunction with a separate filtration or separation device for polymer containing process streams which require a separation device, such as most multi-phase polymer containing process streams. This configuration can increase the lifetime of the bypass filter or other sample preparation device by removing most or all of the particulates from the solution prior to final separation.

Figure 5:
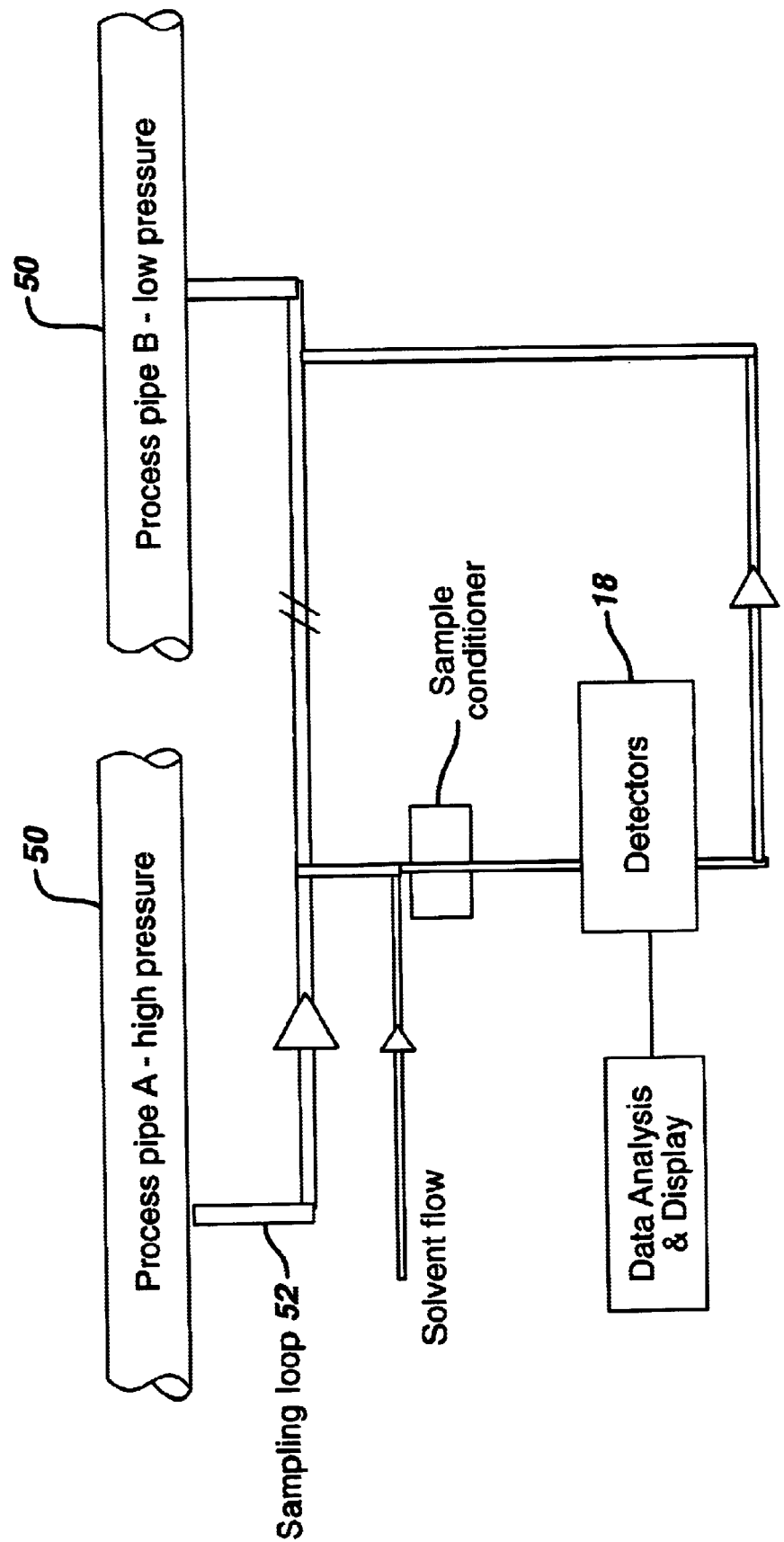
FIG. 5 is schematic diagram of an embodiment of the monitoring system for a polymer containing process stream.

In another embodiment shown in FIG. 5, the apparatus of the present invention is used to monitor a polymer containing process stream. In this embodiment, the polymer containing process stream conduit 50 may have a sampling loop 52 attached to it. A sample of a polymer containing process stream, which often is in the form of a polymer solution and solvent, is introduced to the sample preparation device by a suitable means such as a pump or differential pressure. The diluted solution may also be filtered or degassed. The resulting polymer analyte solution is fed to the detector means 18, and may then be returned to the sampling loop 52. In this embodiment, the polymer containing process stream typically comprises substantially one phase, particularly after dilution. The advantage of utilizing a sampling loop 52 is to reduce the delay time from the polymer containing process stream to the detectors 18.

Figure 6:
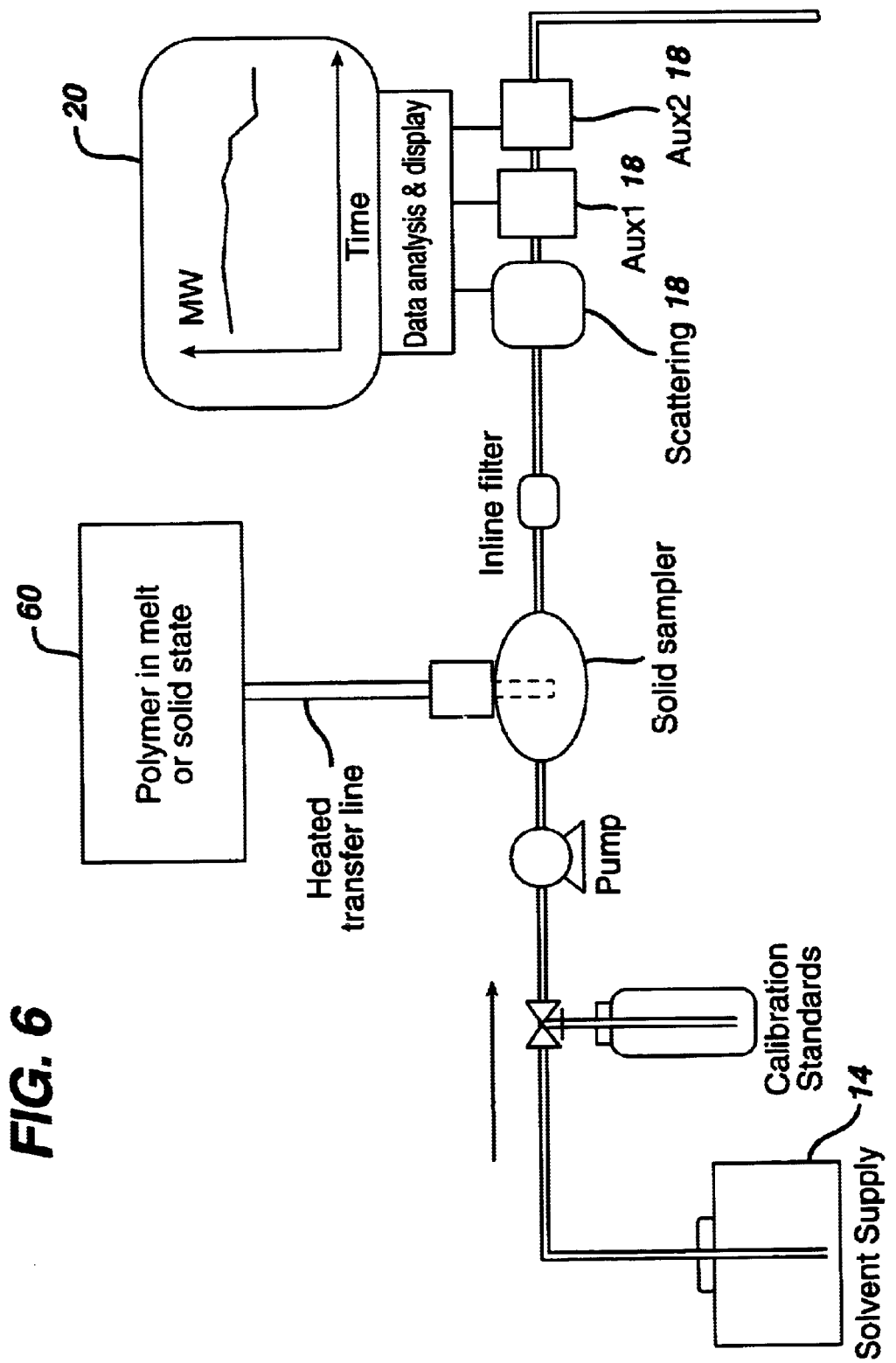
FIG. 6 is schematic diagram of an embodiment of the online monitoring system with a solid sampler.

In yet another embodiment shown in FIG. 6, the apparatus of the present invention is used to monitor solid or melt polymer samples 60 or process streams. In this embodiment, the solid/melt polymer samples 60 are continuously or periodically introduced into a solvent stream where they are dissolved into the solvent, then analyzed by the detectors 18. The solid/melt sample does not have to be totally dissolved because polymer concentration is independently determined.

The present invention is an online, process monitor and method which continuously monitors polymer properties for a polymeric sample from a polymer containing process stream such as reaction mixture from a batch or continuous polymerization reaction, a fluid containing the polymer, or a supply of polymer in melt or solid state. In addition the monitor can detect the reaction endpoint of a polymer manufacturing process. The monitor comprises three major components: a sampling means, a detecting means, and a means for determining polymer weight-average molecular weight and/or size (MWR) as well as identification and/or concentration measurement of selected species associated with the polymer containing process stream based on the response from the detecting means, physical models and calculation software/hardware. The sampling means extracts the analyte (the polymer) from the polymer containing process stream, whether the polymer containing process stream comprises a single phase or two-phase liquid system or a powder or a melt. The dilute analyte solution is then delivered to the detectors. The detecting means comprises a light scattering detector and at least one concentration detector. Each concentration detector determines polymer concentration by UV absorbance or any other suitable means such as, for example, refractive index, fluorescence, acoustic methods, or thermal methods. The light scattering detector measures the intensities of light scattered by the polymer molecules in the solution at one or more scattering angles. The polymer MWR can then be calculated from the light scattering and concentration detector responses. Additional concentration detectors can monitor the concentration of other reaction components, such as free monomer, endgroups, or reaction byproducts. Alternatively, the detector responses can be monitored directly without further calculations for purposes of process monitoring and control.

The monitor has some extremely valuable attributes which represent an advance over the prior art. In particular, the monitor can measure absolute molecular weight rather than a variable which may correlate with molecular weight under special conditions. The monitor is therefore not sensitive to changes in operating conditions such as pH, temperature, pressure, viscosity, phase differences, impurities and so on which affect the reliability of previous methods. Because the monitor detects polymer MWR, and not a unique chemical functionality or a process-specific variable, it is a universal detector, which can monitor the status of polymer containing process streams for all polymers. The monitor thus can be used for any polymerization reaction or polymer containing process stream, including the manufacture of engineering thermoplastics such as polyamides, polyesters, polycarbonates, silicone resins, polyphenylene oxides, polyether imides, poly(butylene terephthalate), poly(ethylene terephthalate), poly(styrene vinylonitrile), Nylons, and biomolecules such as protein and DNA, as well as copolymers and blends.

In a preferred embodiment, the monitor has a rapid response time because it uses a bypass filter sample extraction technique in which a large fraction of the polymer containing process stream flows past the sampling system back to the process, a flow-through detector system, and a light scattering detector which measures one or multiple angles simultaneously. This allows the monitor to rapidly analyze the polymer containing process stream continuously and provide online molecular weight and/or size measurements. This very fast response time allows, for example, detection of the endpoint of the polymerization reaction reliably and quickly, regardless of process conditions. When used to monitor a polymer containing process stream, the monitor allows rapid detection when the manufacturing process develops a problem. In one embodiment, the monitor generates little or no waste because most or all of the sample removed from the polymer containing process stream is returned to the process after analysis. This is possible because for most polymers, only suitable solvent(s) are added to the analyte stream in order to carry out process monitoring.

All of these features combine to produce a monitor which can, for example, accurately detect the reaction endpoint of a polymerization process. The benefits of such a system include, for example, increased reactor productivity by eliminating both off-line analysis and unnecessary reaction time after the endpoint has already been reached, increased reaction product consistency, and reduced raw materials usage.

Figure 7:
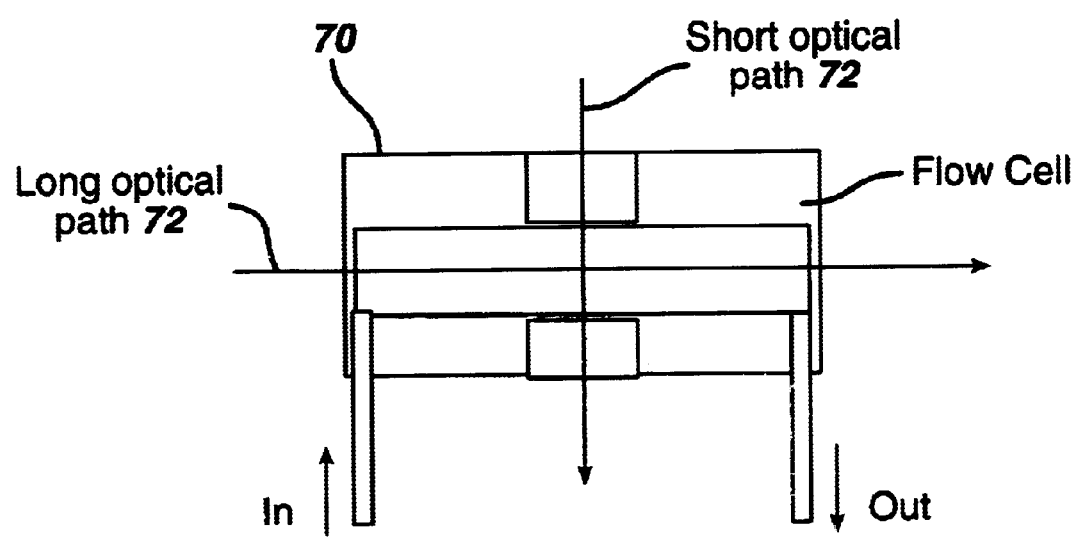
FIG. 7 is a schematic diagram of a flow cell with dual optical path lengths.
Figure 8:
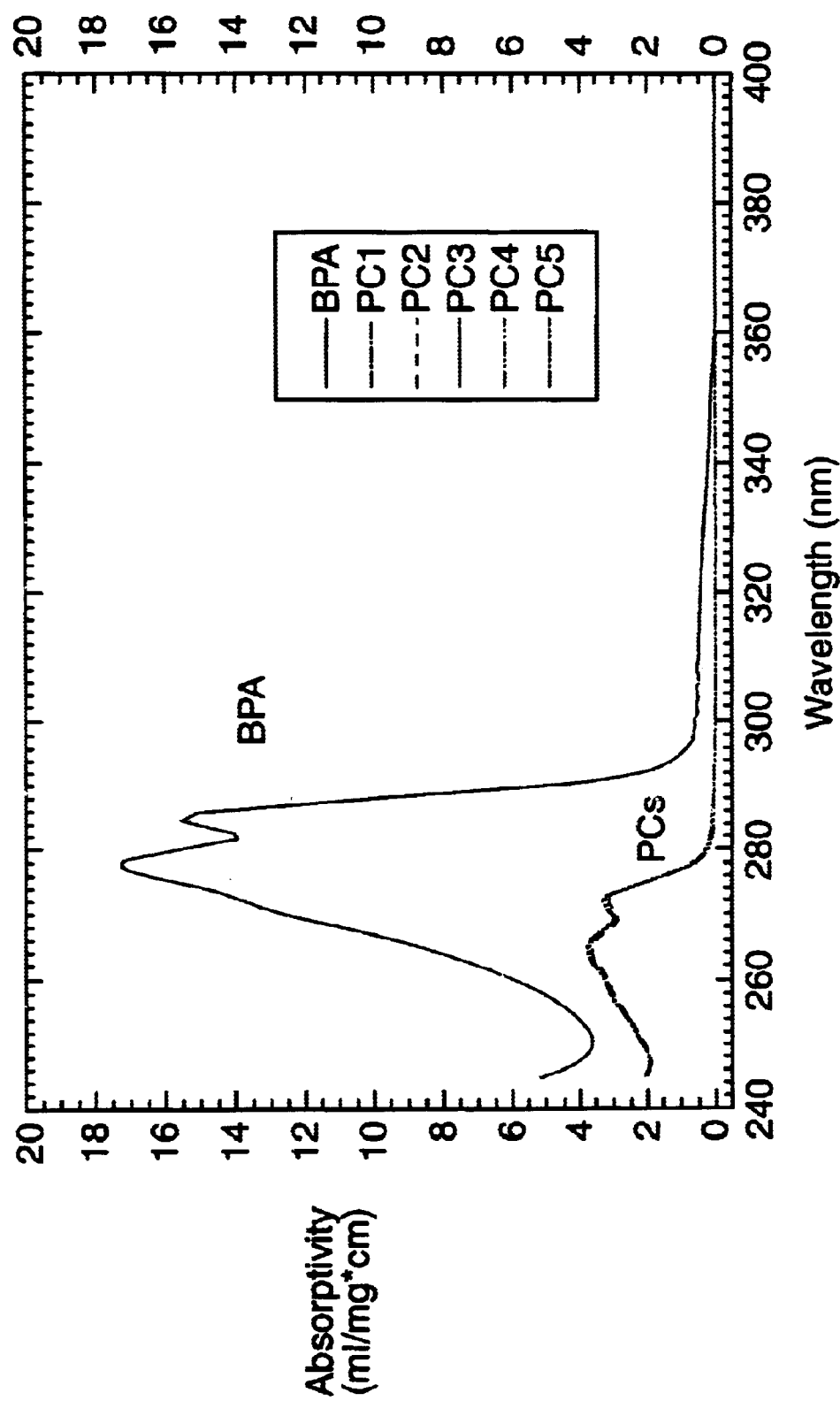
FIG. 8 shows the UV absorbance spectra of BPA and five different grades of polycarbonates.

In a polycarbonate reaction, residual monomer can have a negative impact on polymer quality in concentrations that are too low to measurably affect polymer MWR. To detect low monomer levels, an appropriate detector such as a second UV or UV-visible absorbance detector may be added to the monitor system. Alternatively, a single absorbance detector with a dual optical path flow cell 70 can be used, as shown in FIG. 7. Depending on the spectral properties of the species to be detected with the monitor, various wavelengths and optical path lengths 72 may be used in the detectors. For example, to detect the concentrations of both polycarbonate and BPA monomer, absorbance measurements may be made at two different wavelengths, preferably at 249 nm and 285 nm. The UV absorbance spectra of BPA and polycarbonate grades with weight average molecular weight ranging from 18,000 to 35,000 are shown in FIG. 8. The absorbance spectrum and absorptivity for polycarbonate are essentially independent of weight average molecular weight.

Those skilled in the art can easily provide, based upon the spectroscopic properties of the molecule or molecules to be detected, a detector or detectors with appropriate wavelength settings and optical pathlength to provide absorbance data which will enable an accurate calculation of the concentration(s). A single absorbance detector capable of measuring absorbance at two or more different wavelengths, or multiple single wavelength absorbance detectors may be used to obtain the concentration of two compounds in the analyte solutions. For example, concentration of monomer ($C_M$) and polymer ($C_P$) can be calculated from the following equations, derived from Beer's law once the absorbance values ($A_1$ and $A_2$) at two wavelengths ($\lambda_1$ and $\lambda_2$) are known:

$$A_1 = K_{P-1}C_P + K_{M-1}C_M \quad (1)$$

$$A_2 = K_{P-2}C_P + K_{M-2}C_M \quad (2)$$

Where $K_{P-1}$ and $K_{P-2}$ are the absorbance constants (absorptivity *pathlength) for polymer at the wavelength $\lambda_1$ and $\lambda_2$, and $K_{M-1}$ and $K_{M-2}$ are the absorbance constants for monomer at the wavelength $\lambda_1$ and $\lambda_2$, respectively.

Therefore, $$C_P = (K_{M-1}A_1) - (K_{M-2}A_2)/[(K_{M-1}K_{P-1}) - (K_{M-2}K_{P-2})] \quad (3)$$

$$C_M = 2K_{P-1}A_1 - (K_{P-1}-K_{P-2})A_2 \quad (4).$$

Of course, more than two wavelengths and appropriate equations may be used to measure the concentration of two or more species, such as two distinct monomers and polymer.

When two or more separate detectors are used to make absorbance measurements at two or more different wavelengths, the cells used in each detector may have different pathlengths, allowing independent control of detection sensitivity for each detector. A longer pathlength cell can be used to detect low levels of one component, while a short pathlength cell can be used to detect a component which is relatively concentrated, or which has a high absorbance at the particular desired wavelength. This allows one to control the sensitivity of detection and to avoiding saturating the detector. When a single cell/multiple wavelength detector is used, a compromise typically must be made between the detection limit desired for trace materials, e.g. monomer, and the detector saturation by the more concentrated species, e.g. polymer.

Figure 9:
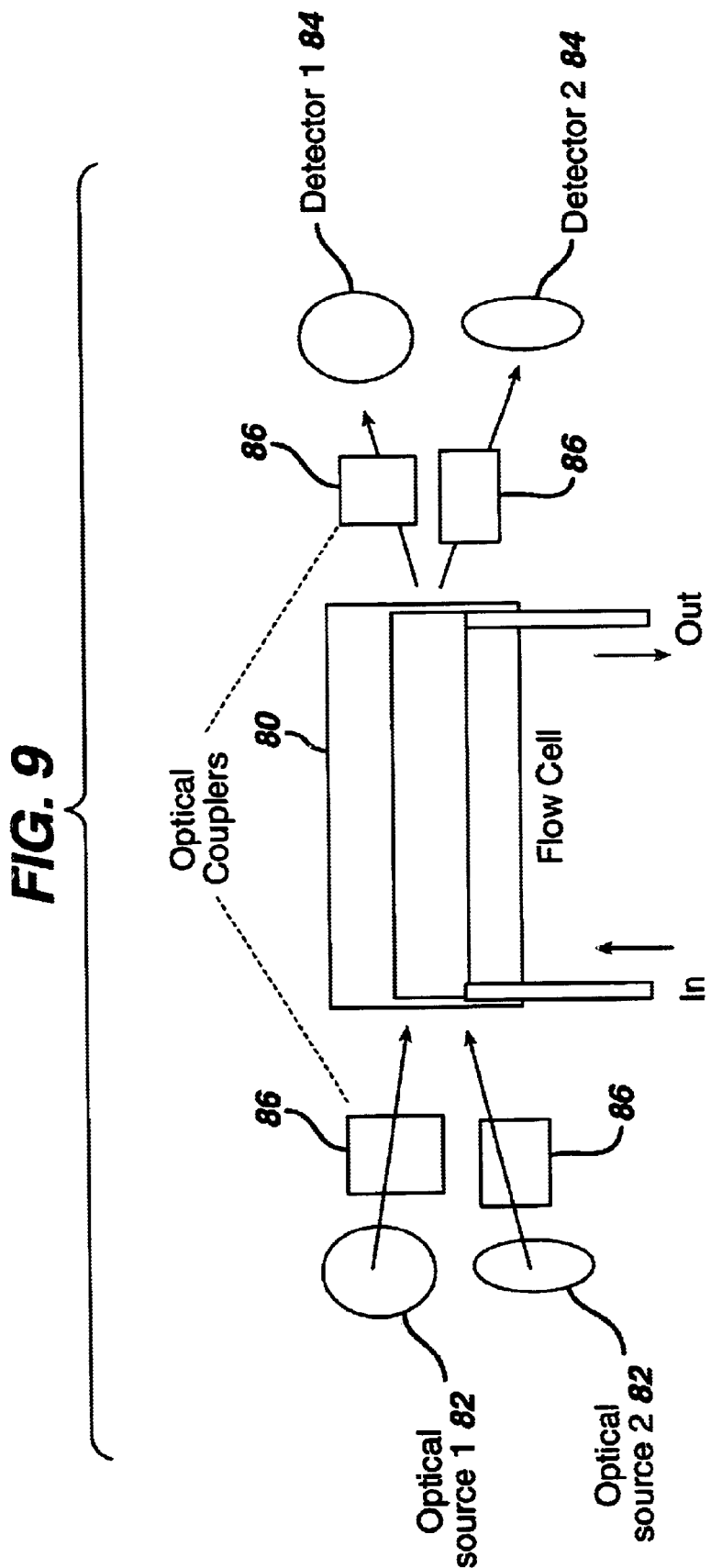
FIG. 9 is a schematic diagram of a single path length flow cell with two separate optical measurement systems.

Another option is to select wavelengths for absorbance measurements which allow the use of one optical pathlength flow cell 80, as depicted schematically in FIG. 9. For example, measuring the absorbance of one compound at a wavelength in the near infrared (NIR) range and the absorbance of another compound in the UV may allow a single pathlength cell 80 to be used for both measurements. A single pathlength flow cell 80 with multiple sources 82, for example a UV source and a NIR source and appropriate detectors 84 using optical coupling devices 86 such as optical fibers for light transmission, is suitable for use in the monitor of this invention.

Because the polymer MWR calculated by the monitor is compensated for the polymer concentration measured at the concentration detector, the monitor does not need to use precisely controlled pumping or flow rates, nor is it essential that the samples from the polymer containing process stream be completely and evenly mixed with the dilution solvent. This is a very important feature of the invention, because, for example, the sampling flow rate may change over the course of a polymerization reaction or because the polymer grade is changed in the polymer containing process stream being monitored.

The light scattering detector measures the light intensities scattered by the analytes at one or more scattering angles. Polymer characterization by light scattering is made possible because large and/or heavy molecules scatter more light than small and/or light molecules. Further, the angular dependence of light scattering is related to the polymer size, as described mathematically by the general light scattering equation (referred as Debye equation,) shown below.

$$\frac{K*C}{R_\theta} = \frac{1}{MW}\left[1 + \left(\frac{16\pi^2 \langle r_g^2 \rangle}{3\lambda^2}\right)\sin^2\left(\frac{\theta}{2}\right)\right] + 2A_2C \quad (5)$$

wherein K*=the optical constant for the particular scattering system determined by solvent optical properties and light frequency; C=polymer concentration; $R_{(\theta)}$=the measured scattering intensity of the solution over that of pure solvent at a given angle; MW=molecular weight; $r_g^2$=mean square radius of gyration; $\lambda$=wavelength; $\theta$=scattering angle and $A_2$=the second viral coefficient which accounts for solvent/solute interaction.

Since light scattering intensity is directly related to the polymer MWR and its measurement is not affected by the presence of other small molecules, such as monomers, catalysts, and endcap molecules, in solution, this makes this method highly suitable for characterization of a variety of polymers under a variety of process conditions. Selection of the light scattering detector portion of the monitor will depend on polymer characteristics and performance requirements. For small polymers with a radius of gyration (a size representation) of less than about 10 nm, multiple angle light scattering detection is not necessary, because in general, polymers with radius of gyration of less than about 10 nm scatter light isotropically (no angular dependence) with common excitation light sources in the visible range; thus accurate molecular size information cannot be calculated from multiple angle detections. For example, polycarbonate with molecular weight of less than 40,000 may be monitored for polymer MWR with a single angle light scattering detector (usually at 90°). Of course, a light scattering detector with multiple angles will improve the measurement precision due to data averaging. In circumstances where molecular size information is needed for molecules with a radius of gyration smaller than about 10 nm, it can be achieved with a dynamic light scattering detector. Thus, one can integrate a dynamic light scattering detector with a regular light scattering detector (also known as steady-state light scattering detector) for the application where accurate molecular weight and size are required.

The molecular weight and/or size of larger molecules can be accurately determined using multiple angle light scattering data. An 18 angle light scattering detector (Model Dawn DSP, Wyatt Technology) equipped with a 632.8 nm laser with 18 geometrically fixed detectors (from 26.6° to 144.5°) is suitable for use in this invention because it can be used for a wide range of polymers. Other light scattering detectors may be used with this invention as is readily apparent to those of ordinary skill in the art. A very low angle detector may be used if it is desirable for the analyte solution to be more concentrated. However, in practice it is more reliable to use the data from dilute analyte solutions rather than from very low angle detectors because the low angle detectors are more susceptible to noise generated by any dust or bubbles remaining in solution.

Light scattering intensity is proportional to the polymer concentration as well as to the polymer size and weight, since the presence of more molecules in solution results in more light scattering. Accurate measurement of concentration is therefore critical. Polymer solution concentration can be measured by a number of methods well known in the art. Commonly used methods are refractive index, absorbance measurements using UV, NIR, IR or visible light, fluorescence, acoustic methods such as ultrasound, or thermal methods such as thermal conductivity. Other potential concentration detectors for polymeric species are chemiluminescence conductivity, electrochemical and heat capacity. The above polymer concentration detection methods are also applicable for monomers, endgroups, by-products and other species of importance to polymer quality. These and any other convenient methods available for accurate and rapid determination of concentration may be used either individually or in combination as part of the monitor system of this invention. Those skilled in the art are able to determine easily which method or methods of concentration determination are suitable for the polymer and solvent system in any particular polymer containing process stream. A preferred concentration detector for use in this invention is a variable wavelength UV absorbance detector with a preparative scale (short optical path length) flow cell. The advantage of using a UV detector rather than a universal detector such as a refractive index detector is that the UV detector is less sensitive to bubbles which may be present in the solution and to the presence of impurities in organic solvents.

The use of online, flow-through detectors is highly preferred for continuous monitoring of polymer containing process streams because it allows a continuous reading to be obtained. Another advantage is that the stream exiting the detector can be directed back into the polymer containing process stream, so that no waste is generated and monitoring results in no loss of material.

A microprocessor-based data analysis and display system such as a computer may be used for data acquisition, storage, analysis, display and transmission for polymer MWR, polymer concentration and other polymer related properties such as identification and quantitation of monomer(s), endgroup (s) and reaction by-product(s). Calculations can be made using a variety of methods, for instance the Debye or Zimm method, based on the light scattering signals from all or some of the detection angles, the measured polymer concentration signals and the responses from additional detectors. By applying the measured polymer concentration and light scattering intensities to the Debye equation or a predetermined model, the polymer MWR and other properties can be obtained. These polymer property values can then be further transformed with signal averaging and trending statistics to provide an actionable information to an operator or a control device.

Similar to the Debye Plot where $R_{(\Theta)}/K*C$ is plotted against $sin^2(\Theta/2)$, the Zimm Plot plots $K*C/R_{(\Theta)}$ versus $sin^2(\Theta/2)+KC$ where K is a constant. The difference between the Debye and the Zimm plot is that the Zimm Plot relies on several high polymer concentrations and the Debye Plot relies on a single low polymer concentration. Either method of calculation may be used with the monitor of this invention.

When using the online monitoring apparatus to detect the endpoint of a batch or continuous polycarbonate polymerization reaction, timely measurements of residual BPA and polycarbonate polymer MWR are of central importance. However, since the dilution factor may vary during the progress of a reaction, the measured BPA concentration can be misleading even though changes in dilution do not affect the calculated molecular weight for the polymer. Therefore, it is preferable under these circumstances to monitor the relative BPA level (the ratio of BPA to polycarbonate) as well as polymer MWR.

To achieve reliable and accurate concentration and light scattering measurements, it is preferable to extract the polymer analyte from the sampling stream as a single phase, remove any particulates which might be present, and present a diluted, bubble-free, representative analyte sample to the detectors, all within a short time.

Depending on the nature and conditions of a polymerization process, the polymer containing process stream may be in a single phase, or in two or more phases. The mixture may contain solids such as catalysts and reactants, or debris such as cellular debris. For example, polycarbonate is polymerized in a water/solvent dispersion that may also contain catalysts, solid BPA, and other materials. A reaction mixture containing a biocatalyst will necessarily contain the cellular biocatalyst and cellular debris.

The sampling means of the present invention thus serves three important functions. First, it separates polymer molecules from the polymer containing process stream (e.g. the two-phase dispersion of an interfacial polycarbonate reaction) to a single solution phase (e.g. the solvent phase for a polycarbonate reaction). Second, it ensures that the analyte solution is very dilute, desirably less than 1 wt % and preferably from about 0.1 wt % to about 0.5 wt % for determination of polyester or polycarbonate molecular weight. For other polymers the appropriate dilution factor for each polymer may be determined by experiment and may be readily determined by one skilled in the relevant art.

Third, it delivers the dilute analyte solution to the concentration and light scattering detectors for analysis.

The first stage in the online molecular weight and/or size monitor is removal of the sample from the polymer containing process stream. Optionally, the sampling means may employ a circulation loop. The circulation loop may be part of the process to be monitored or it may be part of the monitor of this invention. A circulation pump provides fast sample circulation through the loop to help ensure that a representative sample is being removed from the polymer containing process stream. In processes using a biocatalyst or fragile molecules such as DNA, a peristaltic pump may be used to reduce disruption and shear forces. Alternatively, the sample may be removed directly from the polymer containing process stream if a circulation loop is not used.

A sampling pump or other suitable means removes sample material, either from the circulation loop or directly from the polymer containing process stream. The sample is then diluted with a suitable solvent. Precise dilution to a known value is not necessary since the concentration of the polymer is measured at the detectors. The relative flow rates of the sample and the diluent determines the dilution factor. An optimal dilution range may be chosen for the particular process being monitored. This range depends on the characteristics of the separator, the physical and chemical properties of the polymer, and detector sensitivity and linearity. In cases where polymer concentration in a simple one phase process stream is constant and the dilution factor is well controlled, the polymer concentration in the diluted analyte solution can be readily calculated. In such cases, there is no need for polymer concentration detector.

To avoid bubbles in the diluted analyte stream, any suitable means may be used to remove gaseous components from the solvent, for example using an inert, low solubility gas such as helium to sparge the solvent or using an inline degasser.

If necessary, the diluted sample may be subjected to a sample preparation device which is a separation process to remove particulates and to ensure that the sample received by the detectors exists as a single phase. Separations of this kind have been done using, for example, hydrocyclones, continuous centrifuges, bypass phase separation filters, coalescing filters or electrostatic coalescence. Other means to achieve this separation may be apparent to those skilled in the relevant art as well. Any of these means may be used either alone or in combination as part of the monitor of this invention. The sample preparation device yields a filtered and diluted analyte solution, which is then delivered by a suitable flow means such as a pump to the light scattering and concentration detectors. The system optionally also uses a pre-filter or screen to remove particulate matter from the sample solution stream before the stream passes through the sample preparation device. Appropriate valves and mechanisms for back-flushing the sample solution conduits also are desirably included in the system.

For polymer containing process streams which comprise a single liquid phase, a bypass filter which allows a minority of the polymer in solution to pass through the filter, but excludes particulates, catalysts and other materials may be desirable. Filters, suitable for any particular polymer containing process stream will be readily apparent to those skilled in the art. With such a filter, the majority of the reaction stream passes over the filter and back into the circulation loop or directly into the polymer containing process stream being sampled. Thus, the monitor system generates little or no waste material, and removes only a small amount of product from the polymer containing process stream.

After treatment by the sample preparation device, diluted analyte solution is delivered in series or in parallel to light scattering and concentration detectors. A delivery pump optionally may be used to deliver the filtrate solution to these measurement detectors. The concentration detector system which comprises at least one concentration detector determines the total amount of analyte in a unit volume (e.g. mg/ml), while the light scattering detector measures the intensity of scattered light at various angles. Together, they provide calculation of the polymer MWR of the polymer in solution. Since the total analysis time of the on-line molecular weight monitor system is essentially determined by the time required for sampling and delivery to the detectors, low dead volume pumps such as rotary piston pumps supplied by Fluid Metering Inc. are preferably used to minimize the time between sampling and molecular weight calculation.

Figure 10:
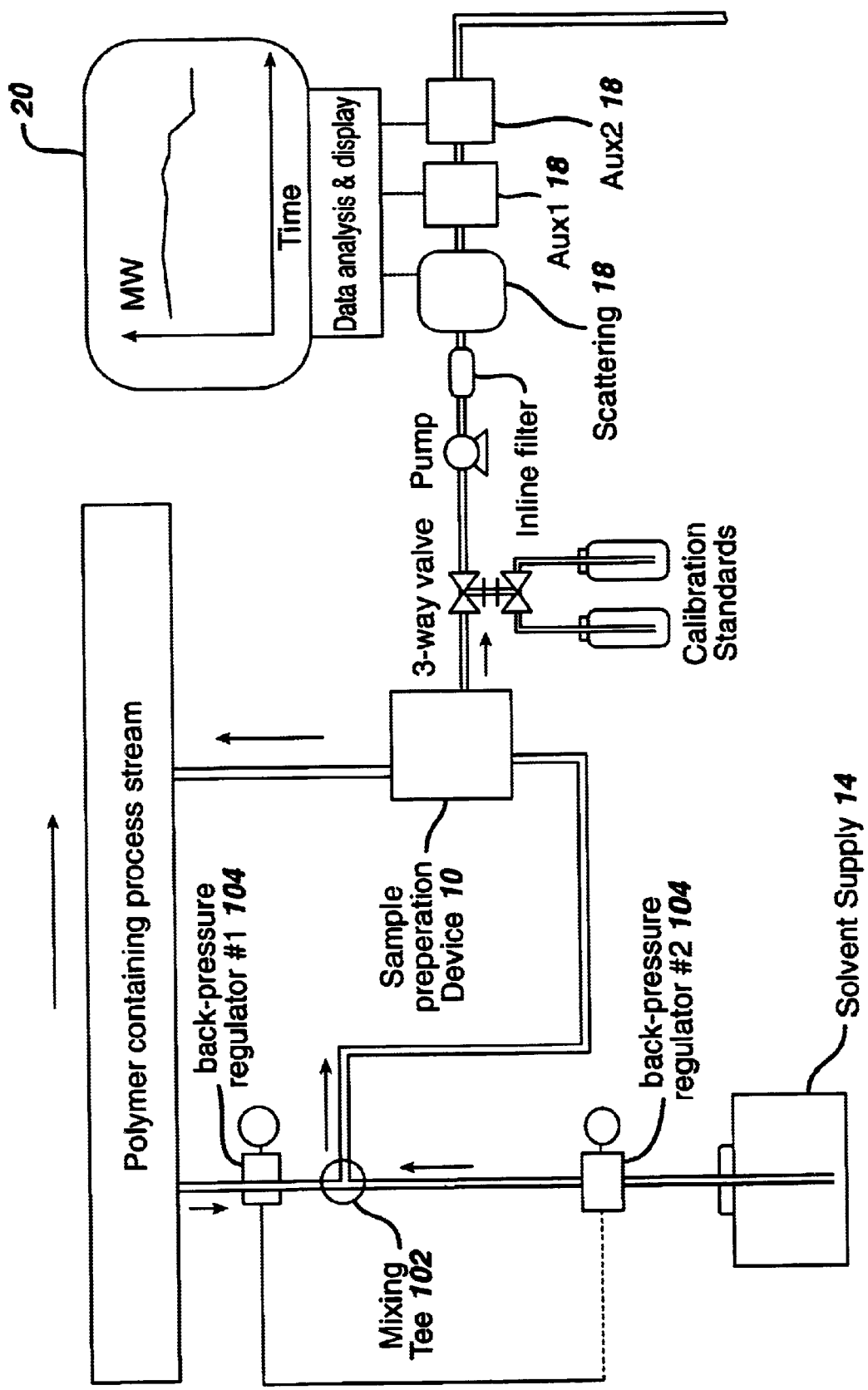
FIG. 10 is a schematic diagram of one embodiment of the apparatus of the present invention with a pressure driven sampling mechanism.

Pressure driven dilution is another alternative to using pumps to deliver the representative sample from the polymer containing process stream and the dilution solvent. Using either the mixing tee 102 or in situ sample probe dilution methods, the flows of each solution may be driven by pressure. FIG. 10 is a diagram of an embodiment of the invention using this principle. In this embodiment, the flows are driven by the pressures of the polymer containing process stream and the solvent supply. The differential pressure between the two streams determines the dilution factor. Each flow rate can optionally be controlled by a suitable control system such as a pressure regulator 104 or control valve. If desired, one regulator can be slaved to the other in order to maintain a constant differential pressure. Of course, depending on the application and process conditions, pressure-driven and pumped systems may be combined.

It is often desirable to control the temperature and/or humidity of the online molecular weight and/or size monitoring apparatus. Therefore, the monitor system is optionally contained within a chamber which is environmentally controlled. Cooling of the system is particularly important when a low-boiling solvent is used or when the ambient temperature becomes elevated. In industry, it is not uncommon for temperatures to become elevated in the area surrounding polymer containing process streams, particularly if polymer containing process stream is part of a polymerization reactor system and if the chemical reaction taking place releases heat. In such cases, the ambient temperature may approach or exceed the boiling point of the solvent, resulting in vaporization of the solvent and the formation of bubbles which can affect the detectors.

Different configurations of the elements of this monitor system will be readily apparent to those of skill in the art. The following nonlimiting examples are provided to illustrate the invention.

EXAMPLE 1

On-line Determination of Molecular Weight During Polycarbonate Reaction Process

A polycarbonate reactor was loaded with 227 g bisphenol A, 1.3 L dichloromethane, 600 mL water, 1.4 mL triethylamine, 139 g paracumyl phenol,. Phosgenation was then begun at about 4 g/minute. Approximately 19.5 minutes after the reaction start, online measurements of molecular weight were begun. Total process time for the reaction was 30 minutes.

The online polymer monitor used a circulation loop and methylene chloride dilution, coupled to a filtering device with Teflon filter elements as shown in FIG. 2. Diluted and filtered solution was directly delivered to a UV detector where the absorbance at 280 nm was measured to give the polymer concentration. Scattered light intensity was measured at 16 scattering angles simultaneously using a Dawn DSP detector (Wyatt Technology Corp.). A portable computer was used to determine the weight-average molecular weight using the Debye equation with the data gathered by the two detectors.

Figure 11:
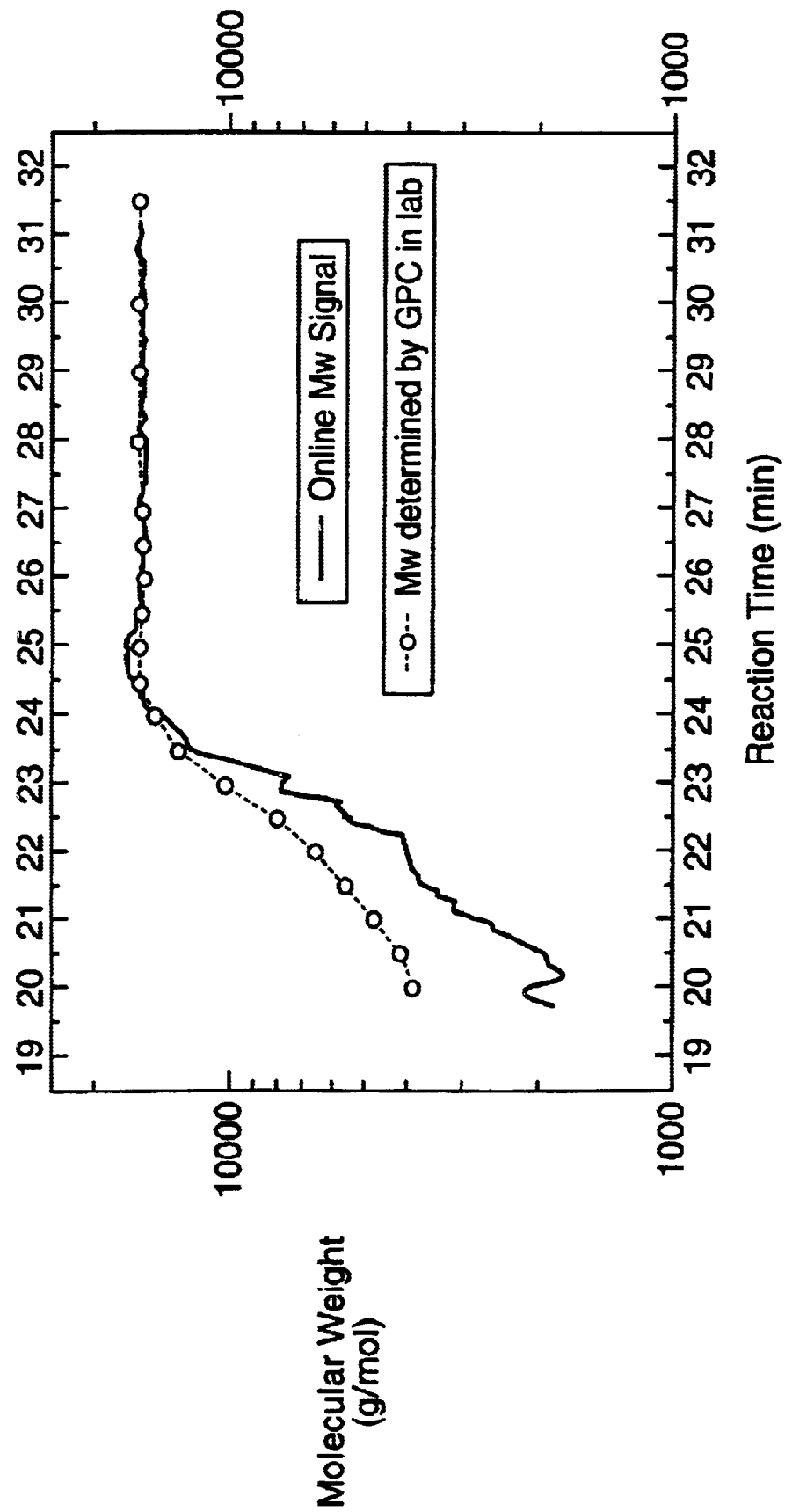
FIG. 11 shows a comparison of molecular weight data taken by the online monitoring system of this invention and off-line GPC data.

To confirm the online molecular weight measurements, the effluent from the online detector was collected for confirmatory analysis rather than being returned to the reactor. Fractions were collected at 30 second intervals into small glass vials and analyzed the same day using a gel permeation chromatography method. The traditional offline analysis of these samples required more than 15 minutes per sample plus additional time for preparation. The analysis time required using the online molecular weight detector was less than 27 seconds. This represents the time from taking the sample from the circulation loop to obtaining a corresponding molecular weight calculation from the computer. Results of the molecular weight monitor for this reaction are given in FIG. 11, with the GPC results for comparison. Results clearly show that the online detector provides an accurate, rapid analysis of the progress of the polycarbonate reaction from which an operator can easily determine the endpoint of the reaction or monitor a polymer containing process stream. It should be noted that the lower molecular weight values determined by the online monitor up to about 23 minutes (compared with the off-line GPC method) is the result of overestimation of the polymer concentration due to absorbance by residual BPA and polymer endgroups that absorb at 280 nm. However, the artificially steep polymer MWR curve may yield a clearer reaction endpoint that that which would be obtained by measuring the polymer concentration in the absence of interference by BPA.

Although this example illustrates the application of the online polymer monitor system for a batch made polymerization reaction, it can also be applied to a step-wide or continuous mode polymerization reaction.

EXAMPLE 2

On-line MW and BPA Determination Using In-situ Sampling Probe

The monitor used in this example comprised an in situ sampling probe with a glass frit (FIG. 4A), a sample bypass filtration unit having two layers of Teflon™-based hydrophobic filter elements, a light scattering detector, two UV absorbance detectors, a three pump solution delivery unit and a computer in the configuration shown in FIG. 3. The light scattering detector was a Dawn DSP detector (Wyatt Technology Corp.). with 18 detection angles. One UV detector (Aux 1) had an optical pathlength of 2.1 mm and was set at a wavelength of 249 mm. The second UV detector had a 10 mm optical pathlength and was set at a wavelength of 285 nm. An in situ sample probe with a built in screen was placed in the solution. The dilution solvent was methylene chloride and the sample solutions were an aqueous brine/methylene chloride mixture prepared by mixing 1L aqueous brine solution (18 wt % NaCl, pH=10.5) with 2L methylene chloride containing various known levels of BPA and polycarbonate. The different polycarbonate/BPA solutions were added to the solution container where the sample probe was located to simulate changes in polycarbonate and BPA concentrations. All sample solutions were stirred moderately so that phase separation did not occur unless stated otherwise.

Figure 12:
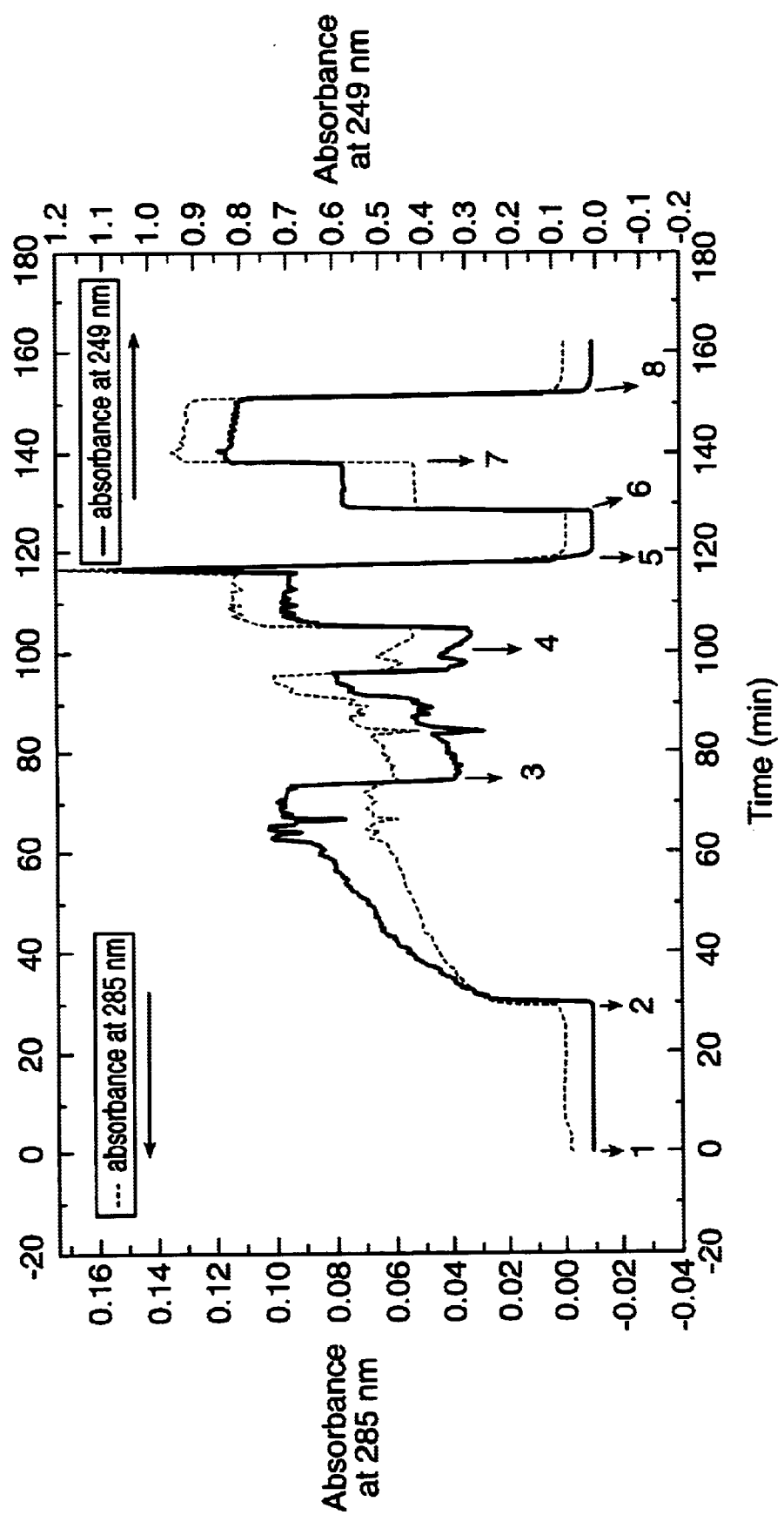
FIG. 12 is a plot of UV absorbance curves versus time two UV detectors with different wavelengths for polycarbonate solutions with various levels of BPA.

FIG. 12 provides the absorbance data from the two UV absorbance detectors, Aux 1 (249 nm) and Aux 2 (285 nm), for eight different sample solutions. At Time Point 1, the experiment started with neither BPA nor polycarbonate in $CH_2Cl_2$. At Time Point 2, the sample solution was switched to a solution containing 8 mg/ml polycarbonate in the $CH_2Cl_2$. At Time Point 3, the sample solution with 30 ppm BPA and 8 mg/ml polycarbonate in $CH_2Cl_2$ was used. At Time Point 4, the same solution was used, but the stirring rate was increased. At Time Point 5, the sample solution having no BPA and polycarbonate in $CH_2Cl_2$ was again used. At Time Point 6, the sample solution used has 6 mg/ml polycarbonate in the $CH_2Cl_2$, but the solution was not stirred so only the organic phase was exposed to the probe. At Time Point 7, the solution with 30 ppm BPA and 8 mg/ml polycarbonate in $CH_2Cl_2$, was again used, again without stirring. At Time Point 8, the solution containing no BPA and polycarbonate in $CH_2Cl_2$ was again used, without stirring.

The sample solution after being diluted in the in-situ probe was pumped into a by-pass filter where two layers of Teflon based hydrophobic filter elements were used. This diluted sample solution still has many water droplets in the $CH_2Cl_2$ phase. The major portion of this diluted sample solution passes by the filter. The gradual absorbance increase for both UV detectors from Time 2 to Time 3 is the result of selective filtration by the glass frit mounted on the probe. Since the glass is hydrophilic, it allows more aqueous solution to pass than the organic phase. As a consequence, polycarbonate and BPA in the sample solution gradually increases as $CH_2C_2$/brine volume ratio increases. This selective filtration behavior can be reduced by using a higher stirring rate, as revealed by much more stable absorbance values after Time Point 4. It is also possible to make an organic selective probe using a hydrophobic screen such as polymer-based frit. The absorbance spikes resulted from sudden changes in the probe position in the vessel.

Figure 13:
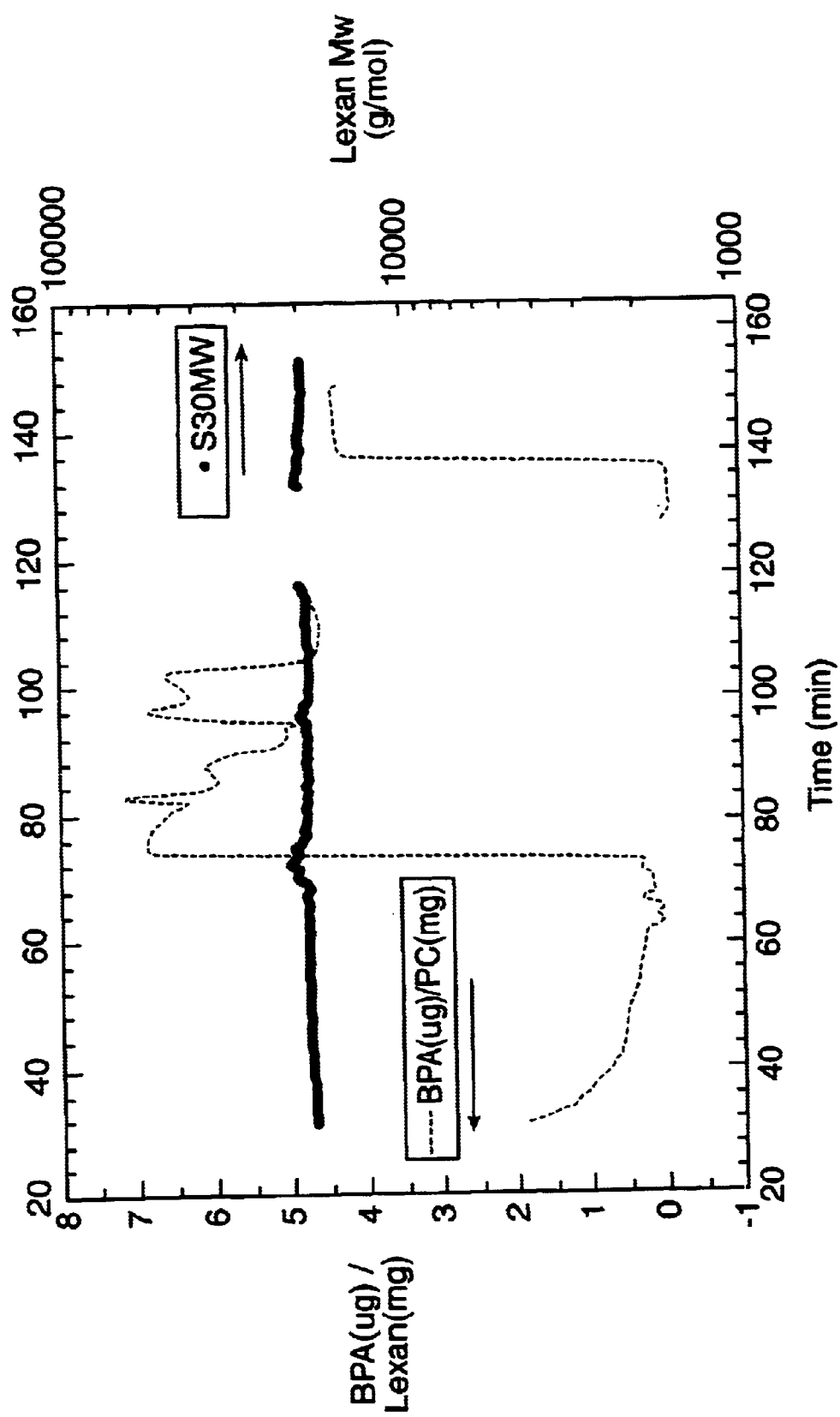
FIG. 13 is a plot of polycarbonate molecular weight and BPA/polycarbonate concentration ratio calculated from the data of FIG. 12.

Based on the absorbance values presented in FIG. 12 and Equations (3) and (4), the online monitor can rapidly and accurately determine the concentrations of polymer and monomer, as displayed in FIG. 13 are the values of their concentration ratio and the polycarbonate molecular weight determined simultaneously based on the polymer concentration measurement and light scattering data. These results agree very well with the known values in the sample solutions. The mean value for the weight-average molecular weight was 19,317 and the relative standard deviation was 2.8%. The detection limit for BPA using this online monitoring apparatus was below 1 ppm in the analyte solution. Therefore, assuming a dilution factor of approximately 20, the detection limit for process samples is less than about 20 ppm.

EXAMPLE 3

Figure 14:
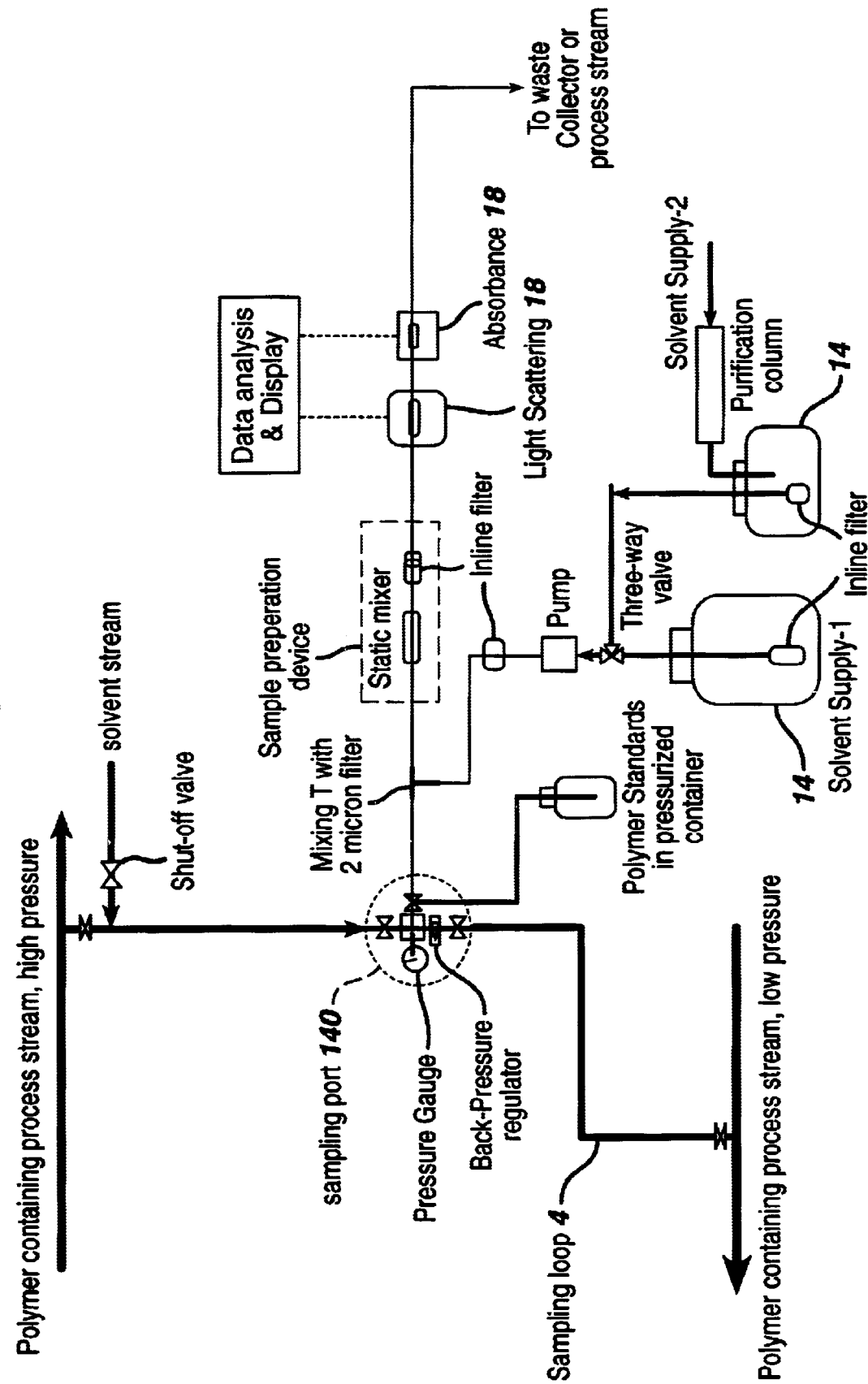
FIG. 14 is a schematic diagram of one embodiment of the apparatus of the present invention used for online MWR monitoring for polymer containing process stream.

FIG. 14 is a schematic diagram of the setup for this test. The online monitoring system was connected to a polycarbonate containing process stream. A sampling loop 4 was installed between the high pressure process stream and an upstream low pressure point. The sample flow rate was controlled by a valve at the sampling port 140. The resin solution was then greatly diluted with HPLC grade methylene chloride. The diluted resin solution was delivered to the detectors 18 for UV absorbance and light scattering measurements. The analyte solution was collected for recycling to the process. The polymer weight average molecular weight and concentration were calculated and displayed on computer screen.

Since the ambient temperature was about 37° C. and because the boiling point for methylene chloride is 40° C., the entire apparatus (except the polycarbonate standard container and the waste collector) was placed inside of an environmental chamber. Due to limitations of the environmental chamber the temperature in the light scattering instrument location cycled from 13.6 to 18.2° C.

Figure 15:
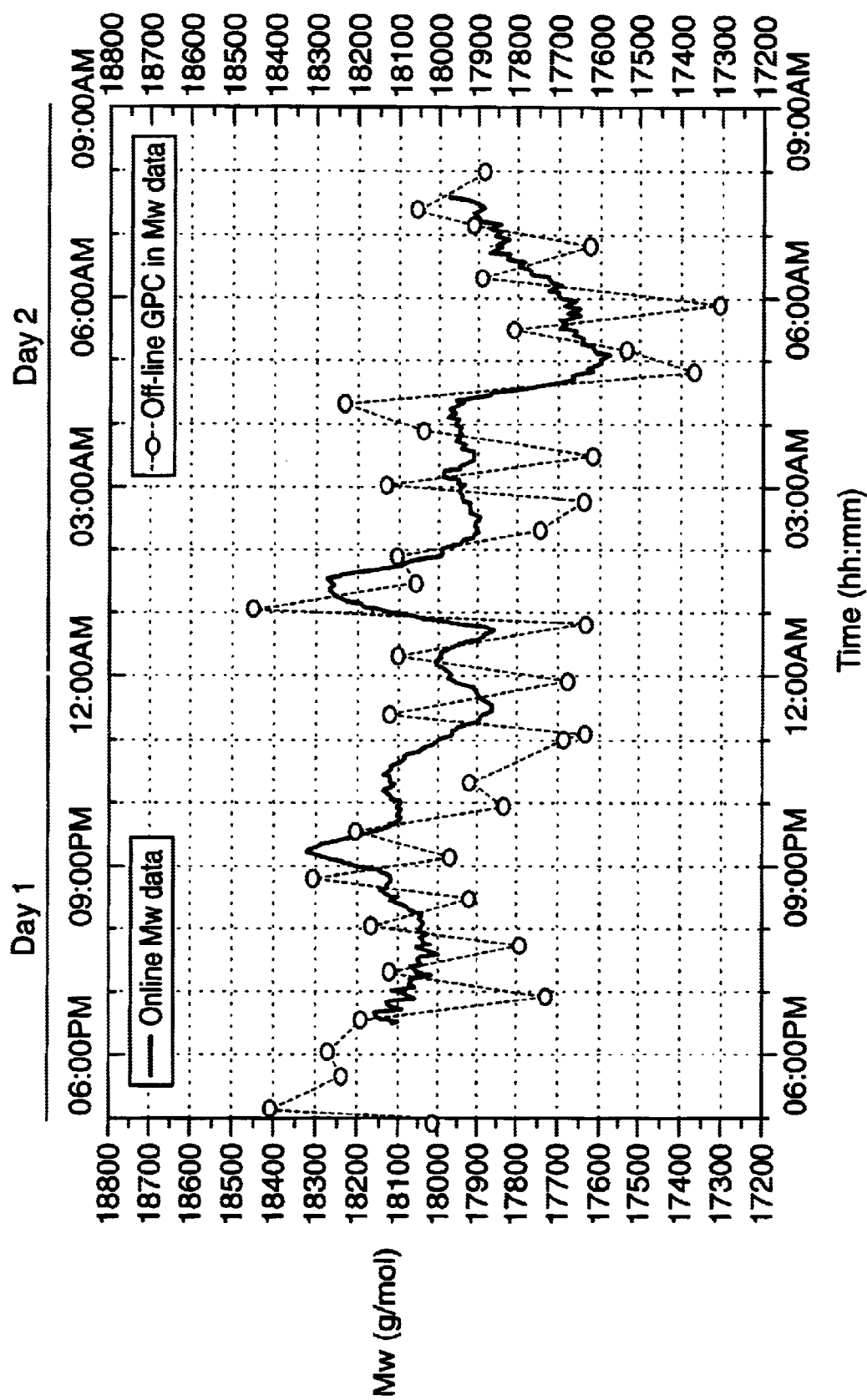
FIG. 15 shows online monitoring system molecular weight data and off-line GPC molecular weight data for a polycarbonate resin stream.

Displayed in FIG. 15 are the Mw values measured with the online system. Displayed online data were smoothed to correct the temperature cycling. The measurements were taken continuously and automatically for more than 14 hours.

For comparison, grab samples from the same polycarbonate process stream were taken, prepared and analyzed at about every 25 minutes by laboratory GPC methods. The GPC weight average molecular weight data are also plotted in FIG. 15. The results clearly reveal that the online polymer weight average molecular weight measurements are within the range of the GPC weight average molecular weight measurements.

EXAMPLE 4

Figure 16:
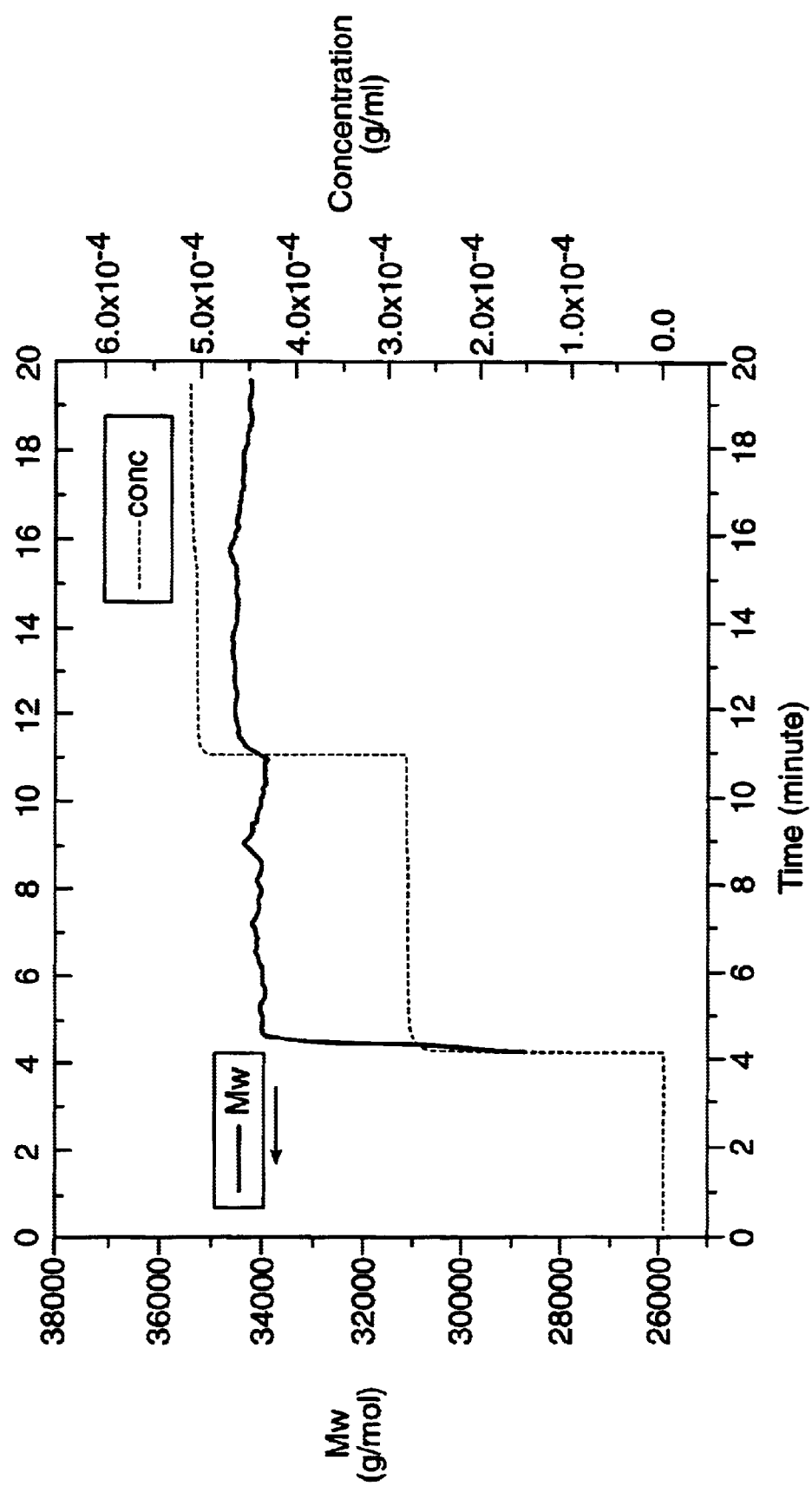
FIG. 16 shows online monitoring system molecular weight data for polyphenylene oxide measurements.

Presented in FIG. 16 are the experimental results obtained with an online monitoring system similar to that shown in FIG. 1. The PPO (polyphenylene oxide) sample solution was diluted with toluene with two different dilution factors, and the diluted PPO solutions were then pumped to the detectors. The light intensities scattered by PPO molecules in the solution are measured at 16 angles. The PPO concentration was measured by absorbance at 300 nm simultaneously with light scattering intensity. Displayed in FIG. 15 are the PPO concentration and its Mw calculated based on the Debye equation against time.

What is claimed is:

1. An online polymer monitoring apparatus for continuous determination of polymer properties, comprising:
   a) a continuous online flow through detector means comprising at least one inlet, one outlet, a steady state light scattering detector, and a polymer concentration detector, said detector means being capable of continuously determining at least one parameter of a polymer-containing sample, said at least one parameter being selected from the group consisting of polymer concentration, polymer molecular weight, molecular size, and concentration of species in said polymer-containing sample;
   b) a continuous sampling and delivery system for continuously collecting a representative. sample from a polymer-containing process stream and continuously delivering the sample to the detector means, said sampling and delivery system comprising a first flow means having a first end connected to the polymer-containing process stream and a second end connected to the detector means inlet; and
   c) a means associated with the flow through detector means for calculating the polymer properties in the representative sample in response to data obtained by said detector means;
wherein the polymer properties are determined at time intervals less than about 30 seconds.

2. An online polymer monitoring apparatus according to claim 1, wherein the calculated polymer properties are selected from the group consisting of polymer molecular weight, polymer molecular size, polymer concentration, and combinations thereof.

3. An online polymer monitoring apparatus according to claim 1, wherein each of the light scattering detector and the polymer concentration detector is selected from the group consisting of separate detectors and an integrated detector system.

4. An online polymer monitoring apparatus according to claim 1, wherein the steady state light scattering detector and the polymer concentration detector are arranged in a configuration selected from the group consisting of series and parallel.

5. An online polymer monitoring apparatus according to claim 1, wherein the concentration detector comprises a light absorbance detector, said absorbance being used to determine said concentration.

6. An online polymer. monitoring apparatus according to claim 5, wherein the absorbance detector is integrated into one absorbance detection unit with a dual optical path flow-cell.

7. An online polymer monitoring apparatus according to claim 6, wherein the detection unit measures absorbance at at least one light wavelength.

8. An online polymer monitoring apparatus according to claim 5, wherein the absorbance detector is integrated into one absorbance detection unit with, single optical path flow-cell measuring absorbance at at least one light wavelength.

9. An online polymer monitoring apparatus according to claim 1, wherein the flow through detector means further comprises at least one additional detector used for identification and quantitation of selected monomers, endgroups, and by-products of polymer reactions in the polymer containing process stream.

10. An online polymer monitoring apparatus according to claim 9, wherein at least one additional detector is integrated into the concentration detector.

11. An online polymer monitoring apparatus according to claim 10, wherein the concentration detector and the at least one additional detector are selected from the group consisting of a UV absorbance detector, a UV-visible absorbance detector, an IR absorbance detector, a visible absorbance detector, a fluorescence detector, an NIR absorbance detector, a refractive index detector, a conductivity detector, an electrochemical detector, thermal capacity, thermal conductivity and an ultrasonic detector, and combinations thereof.

12. An online polymer monitoring apparatus according to claim 1, wherein the polymer-containing process stream comprises a reaction mixture from a batch or continuous polymerization.

13. An online polymer monitoring apparatus according to claim 1, wherein the polymer-containing process stream comprises a fluid containing the polymer.

14. An online polymer monitoring apparatus according to claim 1, wherein the polymer-containing process stream comprises a polymer selected from the group consisting of melt and solid.

15. An online polymer monitoring apparatus according to claim 1, wherein the calculating means comprises a data analysis and transmission system having a microprocessor wherein said microprocessor calculates molecular weight, size based on a predetermined model, a conditioned signal from the at least one detector, and trending statistics, and transmitting information to a device selected from the group consisting of display and a control device.

16. An online polymer monitoring apparatus according to claim 1, wherein the light scattering detector has a single detecting angle.

17. An online polymer monitoring apparatus according to claim 1, wherein the light scattering detector has multiple detecting angles.

18. An online polymer monitoring apparatus according to claim 17, wherein the light scattering detecting angles are different.

19. An online polymer monitoring apparatus according to claim 17, wherein at least two of the light scattering detecting angles are equal.

20. An online polymer monitoring apparatus according to claim 1, wherein the steady state light scattering detector is a multiple-angle steady-state light scattering detector.

21. An on online polymer monitoring apparatus according to claim 1, wherein the light scattering detector is an integration of steady-state and dynamic light scattering detectors.

22. An on online polymer monitoring apparatus according to claim 1, wherein the sampling and delivery s comprises an in situ sampling probe.

23. An online polymer monitoring apparatus according to claim 1, wherein an environment of the apparatus is controlled.

24. An online polymer monitoring apparatus according to claim 1, wherein the sampling and delivery system further comprises a dilution means which comprises a solvent source a second flow means having a first end connected to the solvent source and a second end connected to the first flow means for delivering solvent to the first flow means.

25. An online polymer monitoring apparatus according to claim 24, wherein the dilution means further comprises a mixing means in association with the second flow means.

26. An online polymer monitoring apparatus according to claim 1, wherein the sampling and delivery system further comprises a sample preparation means in association with the first flow means, the sample preparation means preparing an analyte solution from the representative sample by a process selected from the group consisting of diluting the sample with a solvent, separating and filtering interfering materials from the sample, and a combination thereof.

27. An online polymer monitoring apparatus according to claim 26, wherein the sample preparation means comprises a combination of selected sample preparation devices that perform a process selected from the group consisting of phase-separation, filtration, extraction, self-cleaning, and combinations thereof and that have at least an inlet connected to the first flow means and at least a first outlet which leads to the flow through detector.

28. An online polymer monitoring apparatus according to claim 27, wherein the sample preparation means are selected from the group consisting of a bypass filter, a coalescer, a centrifuge, a filter, a degasser, and combinations thereof.

29. An online polymer monitoring apparatus according to claim 27, wherein the sample preparation means further comprises a flow splitter that comprises at least a first outlet and a second outlet, the flow splitter being disposed at a location downstream from the at least an inlet such that a major portion of the material entering the inlet flows out of the second outlet, and a minor portion flows through the filter to the first outlet.

30. An online polymer monitoring apparatus according to claim 26, wherein the sample preparation means is capable of removing particulates, gas bubbles and droplets of a second phase and other interfering materials from the sample.

31. An online polymer monitoring apparatus according to claim 26, further comprising means for maintaining the analyte solution at a substantially constant temperature within a range of temperature below the boiling point of the solvent.

32. An online polymer monitoring apparatus according to claim 1, wherein the sampling and delivery system further comprises a means associated with the first flow means for controlling the flow of the representative sample from the polymer-containing process stream to the detector means.

33. An online polymer monitoring apparatus according to claim 1, wherein the sampling and delivery system further comprises a third flow means for directing material from the outlet of the detector means to the polymer-containing process stream.

34. An online polymer monitoring apparatus according to claim 1, wherein the sampling and delivery system further comprises a circulation loop comprising a fourth flow means between the polymer-containing process stream and the first flow means through which polymer material is moved out of the polymer-containing process stream and returned to the polymer-containing process stream by an action selected from the group consisting of pumping and creating a pressure-differential, and a combination of a pumping and creating a pressure differential in the circulation loop.

35. An online polymer monitoring apparatus for continuous determination of polymer properties, comprising:
   a) a continuous flow through detector means comprising at least one inlet, one outlet, a steady state light scattering detector, and a polymer concentration detector, said detector means being capable of continuously determining at least one parameter of a polymer-containing sample, said at least one parameter being selected from the group consisting of polymer concentration, polymer molecular weight, molecular size, and concentration of species in said polymer-containing sample;
   b) a continuous sampling and delivery system for continuously collecting a representative sample from a polymer-containing process stream and continuously delivering the sample to the detector means, said sampling and delivery system comprising
      (i) a first flow means having a first end connected to the polymer-containing process stream and a second end connected to the detector means inlet;
      (ii) a dilution means which comprises a solvent source a second flow means having a first end connected to the solvent source and a second end connected to the first flow means for delivering solvent to the first flow means;
      (iii) a sample preparation means in association with the first flow means, the sample preparation means preparing an analyte solution from the representative sample by a process selected from the group consisting of diluting the sample with a solvent, separating and filtering interfering materials from the sample, and a combination thereof;
      (iv) a means associated with the first flow means for controlling the flow of the representative sample from the polymer-containing process stream to the detector means; and
      (v) a third flow means for directing material from the outlet of the detector means to the polymer-containing process stream; and
   c) a means associated with the flow through detector means for calculating the polymer properties in the. representative sample in response to data obtained by said detector means;
   wherein the polymer properties are determined at time intervals less than about 30 seconds.

* * * * *